(12) United States Patent
Bauer et al.

(10) Patent No.: US 6,596,509 B1
(45) Date of Patent: Jul. 22, 2003

(54) RECOMBINANT CONSTRUCTS AND SYSTEMS FOR SECRETION OF PROTEINS VIA TYPE III SECRETION SYSTEMS

(75) Inventors: David W. Bauer, Kirkland, WA (US); Steven V. Beer, Ithaca, NY (US); Adam J. Bogdanove, Ithaca, NY (US); Alan Collmer, Ithaca, NY (US); Jong Hyun Ham, Madison, WI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/350,852

(22) Filed: Jul. 9, 1999

Related U.S. Application Data

(60) Provisional application No. 60/092,357, filed on Jul. 10, 1998.

(51) Int. Cl.[7] .................. C12P 21/06; C07H 21/04; C12N 1/21; C12N 15/63; C12N 5/10

(52) U.S. Cl. .................. 435/69.1; 435/6; 435/70.1; 435/71.1; 435/252.3; 435/252.33; 435/320.1; 435/325; 536/23.1; 536/23.4; 536/23.7; 536/24.1; 530/412

(58) Field of Search .................. 536/23.1, 23.4, 536/23.7, 24.1; 435/6, 69.1, 70.1, 71.1, 252.3, 252.33, 320.1, 325; 530/412

(56) References Cited

U.S. PATENT DOCUMENTS

| | | | |
|---|---|---|---|
| 4,757,013 A | 7/1988 | Inouye et al. | 435/172.3 |
| 4,863,855 A | 9/1989 | Inouye et al. | 435/68 |
| 5,223,418 A | 6/1993 | Arcuri et al. | 435/172.3 |
| 5,399,490 A | 3/1995 | Balganesh et al. | |
| 5,552,527 A | 9/1996 | Godiard et al. | 530/379 |
| 5,571,674 A | 11/1996 | Hoshina et al. | 435/6 |
| 5,639,635 A | 6/1997 | Joly et al. | 435/69.1 |
| 5,643,774 A | 7/1997 | Ligon et al. | 435/183 |
| 5,695,958 A | 12/1997 | Builder et al. | 435/69.1 |
| 5,708,139 A | 1/1998 | Collmer et al. | 530/350 |
| 5,716,849 A | 2/1998 | Ligon et al. | 435/419 |
| 5,856,104 A | 1/1999 | Chee et al. | 435/6 |
| 5,891,438 A | 4/1999 | Silverman | 424/185.1 |
| 5,965,381 A | 10/1999 | van der Bruggen et al. | |

FOREIGN PATENT DOCUMENTS

| WO | WO 90/00200 | 1/1990 |
|---|---|---|
| WO | WO 94/09818 | 5/1994 |

OTHER PUBLICATIONS

Puri, N. et al. Molecular Plant–Microbe Interactions 10(2):247–256 (1997).*

McDaniel et al., "A Cloned Pathogenicity Island from Enterpathogenic *Escherichia coli* Confers the Attaching and Effacing Phenotype on *E. Coli* K–12," *Molecular Microbiology* 23(2):399–407 (1997).

Cheng et al., "Two Independent Type III Secretion Mechanisms for YopE in *Yersinia enterocolitica*," *Molecular Microbiology* 24(4):757–765 (1997).

Kim et al., "The *hrpA* and *HrpC* Operons of *Erwinia amylovora* Encode Components of a Type III Pathway That Secretes Harpin," *J. Bacteriology*, 179(5):1690–1697 (1997).

Barny et al., "Cloning of a Large Gene Cluster Involved in *Erwinia amylovora* CFBP1430 Virulence," *Molecular Microbiology*, 4(5):777–786 (1990).

Heu et al., "Nucleotide Sequence and Properties of the *hrmA* Locus Associated with the *Pseudomonas syringae pv. syringae* 61 *hrp* Gene Cluster," *MPMI*, 6(5):553–564 (1993).

Gaudriault et al., "DspA, an Essential Pathogenicity Factor of *Erwinia amylovora* Showing Homology with AvrE of *Pseudomonas syringae*, is Secreted Via the Hrp Secretion Pathway in a DspB–Dependent Way," *Molecular Microbiology*, 26(5):1057–1069 (1997).

Bogdanove et al., "Homology an Functional Similarity of and *hrp*–Linked Pathogenicity Locus, *dspEF*, of *Erwinia amylovora* and the Avirulence Locus *avrE* of *Pseudomonas syringae* Pathovar Tomato," *Proc. Natl. Acad. Sci. USA*, 95:1325–1330 (1998).

Frederick et al., "*Erwinia stewartii* WtsA, a Positive Regulator of Pathogenicity Gene Expression, is Similar to *Pseudomonas syringae* pv. phaseolicola HrpS," *Molecular Microbiology*, 9(3):477–485 (1993).

Gopalan et al., "*hrp* Gene–Dependent Induction of *hin1*: A Plant Gene Activated Rapidly by Both Harpins and the *avrPto* Gene–Mediated Signal," *Plant J.*, 10(4):591–600 (1996).

(List continued on next page.)

*Primary Examiner*—Carla J. Myers
*Assistant Examiner*—Diana Johannsen
(74) *Attorney, Agent, or Firm*—Nixon Peabody LLP

(57) ABSTRACT

One aspect of the present invention relates to a DNA construct that contains a first DNA molecule encoding a functional type III secretion system, a promoter, and a second DNA molecule encoding a protein or polypeptide capable of being secreted by the type III secretion system. The second DNA molecule is operably coupled to the promoter so that upon introduction of the DNA construct into a host cell, the encoded protein or polypeptide and the type III secretion system are expressed and the encoded protein or polypeptide is secreted. Another aspect of the present invention relates to a system that includes (i) a first DNA construct having a first DNA molecule encoding a functional type III secretion system and (ii) a second DNA construct having a promoter operably coupled to a second DNA molecule encoding a protein or polypeptide capable of being secreted by the type III secretion system. Upon introduction of the first and second DNA constructs into a host cell, the encoded protein or polypeptide and the type III secretion system are expressed and the encoded protein or polypeptide is secreted. Methods of isolating a protein or polypeptide and identifying a gene encoding a potential effector protein or polypeptide are also disclosed.

91 Claims, 8 Drawing Sheets

OTHER PUBLICATIONS

Leach et al., "Bacterial Avirulence Genes,"*Annu. Rev. Phytophol.,* 34:153–179 (1996).

Reverchon et al., "Cloning of Genes Encoding Pectolytic Enzymes from a Genomic Library of the Phytopathogenic Bacterium, *Erwinia chrysanthemi,*" *Gene,* 35:121–130 (1985).

Keen et al., "Structure of Two Pectate Lyase Genes from *Erwinia chrysanthemi* EC16 and Their High–Level Expression in *Escherichia coli,*" *Journal of Bacteriology,* 168(2):595–606 (1986).

Scheu et al., "Secretion of the *Rhizobium leguminosarum* Nodulation Protein NodO by Haemolysin–Type Systems," *Molecular Microbiology,* 6(2):231–238 (1992).

Rezaie et al., "Expression and Purification of a Soluble Tissue Factor Fusion Protein with an Epitope for an Unusual Calcium–Dependent Antibody," *Protein Expression and Purification,* 3:453–460 (1992).

Sory et al, "Identification of the YopE and YopH Domains Required for Secretion and Internalization into the Cytosol of Macrophages, Using the *cyaA* Gene Fusion Approach," *Proc. Nat'l. Acad. Sci. USA,* 92:11998–12002 (1995).

Savijoki et al., "High Level Heterologous Protein Production in *Lactococcus* and *Lactobacillus* Using a New Secretion System Based on the *Lactobacillus brevis* S–Layer Signal," *Gene,* 186:255–262 (1997).

Bogdanove, et al., "*Erwinia amylovora* Secretes DspE, a Pathogenicity Factor and Functional AvrE Homolog, Through the Hrp (Type III Secretion) Pathway," *J. Bacteriol.,* 180(8):2244–2247 (1998).

Anderson, et al, "A mRNA Signal for the Type III Secretion of Yop Proteins by *Yersinia enterocolitica,*" *Science,* 278:1140–43 (1997).

Montag et al., "Receptor–recognizing Proteins of T–even Type Bacteriophages: Constant and Hypervariable Regions and An Unusual Case of Evolution,"*J. Mol. Biol.* 196:165–174 (1987).

Moncla et al., "Use of Synthetic Oligonucleotide DNA Probes for Identification and Direct Detection of *Bacteroides forsythus* in Plaque Samples," *Journal of Clinical Microbiology,*29(10):2158–2162 (1991).

Sheiness et al., "High Levels of *Gardnerella vaginalis* Detected with an Oligonucleotide Probe Combined with Elevated pH as a Diagnostic Indicator of Bacterial Vaginosis,"*Journal of Clinical Microbiology* 30(3):642–648 (1992).

Spierings et al., "Polymerase Chain Reaction for the Specific Detection of *Escherichia coli/Shigella,*" *Res. Microbiol.* 144:557–564 (1993).

Pear et al., "Higher Plants Contain Homologs of the Bacterial *celA* Genes Encoding the Catalytic Subunit of Cellulose Synthase," *Proc. Natl. Acad. Sci. USA* 93:12637–12642 (1996).

Mansfield et al., "Characterization of *avrPphE,* a Gene for Cultivar–Specific Avirulence from *Pseudomonas syringae pv. phaseolicola* Which is Physically Linked to *hrpY,* a New *hrp* Gene Identified in the Halo–Blight Bacterium," *MPMI* 7(6) 726–739 (1994).

Cornelis et al., The *Yersinia* Yop Virulon: A Bacterial System for Subverting Eukaryotic Cells, *Molecular Microbiology* 23(6):861–867 (1997).

J. E. Galán, "'Avirulence Genes' in Animal Pathogens?," *Trends in Microbiology* 6(1):3–6 (1998).

Alfano et al., "Bacterial Pathogens in Plants: Life up Against the Wall," *The Plant Cell* 8:1683–1698 (1996).

Ham et al., "A Cloned *Erwinia chrysanthemi* Hrp (Type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA* 95:10206–10211 (1998).

Galán et al., "Type III Secretion Machines: Bacterial Devices for Protein Delivery into Host Cells," *Science* 284:1322–1328 (1999).

A. Collmer, "Determinants of Pathogenicity and Avirulence in Plant Pathogenic Bacteria," *Current Opinion in Plant Biology* 1:329–335 (1998).

A. Charkowski, "*Pseudomonas Syringae Hrp* Gene Pathogencity Islands," A Dissertation Presented to the Faculty of the Graduate School of Cornell University, Chapter 3, pp. 56–89 (catalogued Jan. 1999).

\* cited by examiner

IMMUNOBLOTS OF DspE IN SUPERNATANT AND CELL FRACTIONS FROM E. AMYLOVORA GROWN IN HRP INDUCING MEDIUM

LANE 1. Hrp MUTANT Ea273-K178.
LANE 2. WILD-TYPE STRAIN Ea273.
LANE 3. PARTIAL dspE DELETION MUTANT STRAIN Ea273dspE $^2$1521.

FIG. 6

SEQUENCE LISTING

<160> NUMBER OF SEQ ID NOS: 6

<210> SEQ ID NO 1
<211> LENGTH: 201
<212> TYPE: PRT
<213> ORGANISM: Erwinia amylovora

<400> SEQUENCE: 1

```
Met Glu Leu Lys Ser Leu Gly Thr Glu His Lys Ala Ala Val His Thr
 1               5                  10                  15

Ala Ala His Asn Pro Val Gly His Gly Val Ala Leu Gln Gln Gly Ser
             20                  25                  30

Ser Ser Ser Ser Pro Gln Asn Ala Ala Ala Ser Leu Ala Ala Glu Gly
         35                  40                  45

Lys Asn Arg Gly Lys Met Pro Arg Ile His Gln Pro Ser Thr Ala Ala
     50                  55                  60

Asp Gly Ile Ser Ala Ala His Gln Gln Lys Lys Ser Phe Ser Leu Arg
 65                  70                  75                  80

Gly Cys Leu Gly Thr Lys Lys Phe Ser Arg Ser Ala Pro Gln Gly Gln
                 85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140
```

Ala Gly Arg Pro Met Val Lys Gly Gly Ser Gly Glu Asp Lys Val Pro
145                 150                 155                 160

Thr Gln Lys Arg His Gln Leu Asn Asn Phe Gly Gln Met Arg Gln
            165                 170                 175

Thr Met Leu Ser Lys Met Ala His Pro Ala Ser Ala Asn Ala Gly Asp
        180                 185                 190

Arg Leu Gln His Ser Pro Pro His Ile
        195                 200

```
<210> SEQ ID NO 2
<211> LENGTH: 603
<212> TYPE: DNA
<213> ORGANISM: Erwinia amylovora

<400> SEQUENCE: 2
atggaattaa aatcactggg aactgaacac aaggcggcag tacacacagc ggcgcacaac      60
cctgtggggc atggtgttgc cttacagcag ggcagcagca gcagcagccc gcaaaatgcc     120
gctgcatcat tggcggcaga aggcaaaaat cgtgggaaaa tgccgagaat tcaccagcca     180
tctactgcgg ctgatggtat cagcgctgct caccagcaaa agaaatcctt cagtctcagg     240
ggctgtttgg ggacgaaaaa attttccaga tcggcaccgc agggccagcc aggtaccacc     300
cacagcaaag gggcaacatt gcgcgatctg ctggcgcggg acgacggcga acgcagcat      360 gaggcggccg cgccagatgc ggcgcgtttg acccgttcgg gcggcgtcaa cgccgcaat     420 atggacgaca tggccgggcg gccaatggtg aaaggtggca gcggcgaaga taaggtacca     480
acgcagcaaa aacggcatca gctgaacaat tttggccaga tgcgccaaac gatgttgagc     540
aaaatggctc acccggcttc agccaacgcc ggcgatcgcc tgcagcattc accgccgcac     600
atc                                                                   603

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 3
agatctgatc aagagacag                                                   19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 4
ccgtgtgtat aagagtcag                                                   19

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 5
gagcgagcat atgggaaata tatgtgtcgg c                                     31
```

```
-continued

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:  primer

<400> SEQUENCE: 6
attgtagtcg acttgccagt tacggtacgg g                                          31
```

RECOMBINANT CONSTRUCTS AND SYSTEMS FOR SECRETION OF PROTEINS VIA TYPE III SECRETION SYSTEMS

This application claims the benefit of U.S. Provisional Patent Application Serial No. 60/092,357, filed July 10, 1998.

This invention was made in part with support by the U.S. Government under Grant No. MCB-9631530 from National Science Foundation and Grant No. 97-35303-4488 from the U.S. Department of Agriculture, NRI Competitive Grants Program. The U.S. Government may have certain rights in this invention.

DESCRIPTION OF DEPOSITED BIOLOGICAL MATERIALS

The biological material listed below has been deposited with the American Type Culture Center (10801 University Blvd., Manassas, Va.):

| ATCC Deposit No. | Description | Date Deposited |
| --- | --- | --- |
| PTA-3287 | Escherichia coli containing the cloned hrp gene cluster of Erwinia chrysanthemi: DH5α(pCPP2156) | Apr. 13, 2001 |
| PTA-3288 | Escherichia coli containing the cloned hrp gene cluster of Erwinia amylovora: DH5(pCPP430) | Apr. 13, 2001 |

BACKGROUND OF THE INVENTION

The most common bacterial pathogens of plants colonize the apoplast, and from that location outside of the walls of living cells they incite a variety of diseases in most cultivated plants (Alfano et al., "Bacterial Pathogens in Plants: Life Up Against the Wall," *Plant Cell* 8:1683–1698 (1996)). The majority of these are Gram-negative bacteria in the genera Erwinia, Pseudomonas, Xanthomonas, and Ralstonia. Most are host specific and will elicit the hypersensitive response ("HR") in nonhosts. The HR is a rapid, programmed death of plant cells in contact with the pathogen. Some of the defense responses associated with the HR are localized at the periphery of plant cells at the site of bacterial contact, but what actually stops bacterial growth is not known (Brown et al., "hrp genes in *Xanthomonas campestris* pv. *vesicatoria* Determine Ability to Suppress Papilla Deposition in Pepper Mesophyll Cells," *MPMI* 8:825–836 (1995); Young et al., "Changes in the Plasma Membrane Distribution of Rice Phospholipase D During Resistant Interactions With *Xanthomonas oryzae* pv. *oryzae*," *Plant Cell* 8:1079–1090 (1996); Bestwick et al., "Localization of Hydrogen Peroxide Accumulation During the Hypersensitive Reaction of Lettuce Cells to *Pseudomonas syringae* pv. *phaseolicola*," *Plant Cell* 9:209–221 (1997)). Pathogenesis in host plants, in contrast, involves prolonged bacterial multiplication, spread to surrounding tissues, and the eventual production of macroscopic symptoms characteristic of the disease. Although these bacteria are diverse in their taxonomy and pathology, they all possess hrp genes which direct their ability to elicit the HR in nonhosts or to be pathogenic (and parasitic) in hosts (Lindgren, "The Role of hrp Genes During Plant-Bacterial Interactions," *Annu. Rev. Phytopathol.* 35:129–152 (1997)). The hrp genes encode a type III protein secretion system that appears to be capable of delivering Avr (avirulence) proteins across the walls and plasma membranes of living plant cells (Alfano et al., "The Type III (Hrp) Secretion Pathway of Plant Pathogenic Bacteria: Trafficking Harpins, Avr Proteins, and Death," *J. Bacteriol.* 179:5655–5662 (1997), which is hereby incorporated by reference). The Avr proteins are so named because they can betray the parasite to the R gene-encoded surveillance system of plants, thereby triggering the HR (Vivian et al., "Avirulence Genes in Plant-Pathogenic Bacteria: Signals or Weapons?," *Microbiology* 143:693–704 (1997); Leach et al., "Bacterial Avirulence Genes," *Annul. Rev. Phytopathol.* 34:153–179 (1996)). But Avr-like proteins also appear to be key to parasitism in compatible host plants, where the parasite proteins are undetected and the HR is not triggered. Thus, bacterial avirulence and pathogenicity are interrelated phenomena and explorations of HR elicitation are furthering our understanding of parasitic mechanisms.

Despite the emerging importance of Avr proteins, there is no direct evidence that they travel the Hrp pathway, there is no knowledge of their function in virulence, it appears likely that only a subset of those that are produced by typical host-specific pathogens have been identified, and there is no evidence that they are produced at all by host-promiscuous pathogens. The evidence that Avr proteins are transferred by the Hrp pathway into plants is most complete, although still indirect, with *Pseudomonas syringae* AvrB and AvrPto proteins. Nonpathogenic *Escherichia coli* and *Pseudomonas fluorescens* cells that harbor the functional cluster of *Pseudomonas syringae* hrp genes carried on cosmid pHIR11 can elicit an HR that is dependent on both the type III secretion system and either AvrB or AvrPto (Gopalan et al., "Expression of the *Pseudomonas Syringae* Avirulence Protein AvrB in Plant Cells Alleviates its Dependence on the Hypersensitive Response and pathogenicity (Hrp) Secretion System in Eliciting Genotype-specific Hypersensitive Cell Death," *Plant Cell* 8:1095–1105 (1996); Pirhonen et al., "Phenotypic Expression of *Pseudomonas Syringae* avr Genes in *E. coli* is Linked to the Activities of the hrp-encoded Secretion System," *MPMI* 9:252–260 (1996)). Both Avr proteins trigger an R gene-dependent HR when transiently expressed inside plant cells (Gopalan et al., "Expression of the *Pseudomonas Syringae* Avirulence Protein AvrB in Plant Cells Alleviates its Dependence on the Hypersensitive Response and pathogenicity (Hrp) Secretion System in Eliciting Genotype-specific Hypersensitive Cell Death," *Plant Cell* 8:1095–1105 (1996)) and the interaction of AvrPto and Pto in the yeast two-hybrid system correlates with biological activity (Tang et al., *Science* 274:2060 (1996); Scofield et al., *Science* 274:2063–2065 (1996)). However, neither *Pseudomonas syringae, Escherichia coli* (pHIR11), nor *Pseudomonas fluorescens* (pHIR11) secrete AvrB or AvrPto in culture, presumably because these proteins travel the type III pathway directly into host cells and only upon host cell contact, as with the Yop virulence proteins of Yersinia spp. (Gopalan et al., "Expression of the *Pseudomonas syringae* Avirulence Protein AvrB in Plant Cells Alleviates its Dependence on the Hypersensitive Response and Pathogenicity (Hrp) Secretion System in Eliciting Genotype-specific Hypersensitive Cell Death," *Plant Cell* 8:1095–1105 (1996); Cornelis et al., "The Yersinia Yop Regulon: A Bacterial System for Subverting Eukaryotic Cells," *Mol. Microbiol.* 23:861–867 (1997)). Other known Avr proteins have been observed only in the bacterial cytoplasm (Leach et al., "Bacterial Avirulence Genes," *Annu. Rev. Phytopathol.* 34:153–179 (1996); Knoop et al., "Expression of the Avirulence Gene avrBs3 from *Xanthomonas campestris* pv. *vesicatoria* is not Under the Control of hrp Genes and is Independent of Plant Factors," *J. Bacteriol.* 173:7142–7150 (1991); Puri et al., "Expression of avrPphB, an Avirulence Gene from *Pseudomonas Syringae* pv. Phaseolicola, and the Delivery of Signals Causing the Hypersensitive Reaction in Bean," *MPMI* 10:247–256 (1997)).

Many proteins and polypeptides, including hormones and enzymes, are in high demand for pharmacological and industrial use. Once the gene encoding a desired protein or polypeptide has been isolated, the protein can be produced readily through fermentation in rapidly growing bacteria. *Escherichia coli* is used most commonly for large-scale protein production. Current technology enables the production of relatively large intracellular concentrations of the desired proteins or polypeptides. Extraction of the desired protein or polypeptide from the bacterial cells requires lysing of the cell membrane. After lysing the cell membrane, the desired protein or polypeptide is contaminated with other proteins and, therefore, subject to degradation. The resulting contamination requires significant purification to obtain the isolated protein or polypeptide and degradation of the desired protein or polypeptide limits the obtainable yield.

In addition to fermentation technologies for production of proteins or polypeptides, gene therapy involving transgenic plants is emerging as an important tool for enhancing agricultural productivity and reducing disease losses. For example, transgenic plants expressing bacterial and viral proteins are now used for herbicide tolerance and resistance to viral diseases, respectively. Because of the ease with which foreign proteins can be expressed in most major crops, it is feasible to bioprospect for proteins that will alter plant metabolism to enhance productivity and prevent losses due to pests.

Phytopathogenic bacteria contain a reservoir of genes encoding proteins that have evolved to be biologically active inside plants. Although poorly understood at this point, these proteins are likely to alter plant growth and development, affect fundamental cellular processes common to all higher organisms, including both plants and animals, and/or interact with defense mechanisms. The reservoir of these genes is potentially large, but only a relatively small number have been identified among all of the phytopathogenic bacteria, because identifying them has been dependent upon inefficient procedures involving transgenic pathogens, plant inoculations, and plant reactions.

Thus, it would be beneficial to obtain a recombinant construct and expression system which overcomes these and other deficiencies in the art, particularly the ability to produce a recombinant host organism capable of expressing and secreting Avr and/or other desired proteins or polypeptides into their environment (i.e., culture medium).

SUMMARY OF THE INVENTION

One aspect of the present invention relates to a DNA construct that contains a first DNA molecule encoding a functional type III secretion system, a promoter, and a second DNA molecule encoding a protein or polypeptide capable of being secreted by the type III secretion system. The second DNA molecule is operably coupled to the promoter so that upon introduction of the DNA construct into a host cell, the encoded protein or polypeptide and the type III secretion system are expressed and the encoded protein or polypeptide is secreted. Also disclosed are host cells and expression systems that contain the DNA construct, as well as a method of secreting a protein or polypeptide into the environment of a host cell which employs the DNA construct.

Another aspect of the present invention relates to a system that includes a (i) first DNA construct having a first DNA molecule encoding a functional type III secretion system and (ii) a second DNA construct having a promoter operably coupled to a second DNA molecule encoding a protein or polypeptide capable of being secreted by the type III secretion system. Upon introduction of the first and second DNA constructs into a host cell, the encoded protein or polypeptide and the type III secretion system are expressed and the encoded protein or polypeptide is secreted. Also disclosed are host cells and expression systems that contain the system of DNA constructs, as well as a method of secreting a protein or polypeptide into the environment of a host cell which employs the system of DNA constructs.

A further aspect of the present invention relates to a method of isolating a protein or polypeptide. This method is performed by providing a recombinant host cell that contains (i) a first DNA molecule encoding a functional type III secretion system and (ii) a second, heterologous DNA molecule having a promoter operably coupled to a nucleic acid sequence encoding a protein or polypeptide capable of being secreted by the type III secretion system. The recombinant host cell is introduced into a culture medium, wherein the encoded protein or polypeptide and the type III secretion system are expressed and the encoded protein or polypeptide is secreted into the culture medium. Subsequently, the encoded protein or polypeptide is isolated from the culture medium.

Still another aspect of the present invention relates to a method of identifying a gene encoding a potential effector protein or polypeptide. This method of the invention is performed by providing a host cell that contains a DNA molecule encoding a functional type III secretion system. Next, a candidate gene encoding a protein or polypeptide is inserted into the host cell under conditions effective to express the encoded protein or polypeptide. Finally, it is determined whether the encoded protein or polypeptide is secreted by the recombinant host cell, wherein secretion of the encoded protein or polypeptide indicates that the gene encodes a potential effector protein or polypeptide.

Since the DNA constructs of the present invention enable expression and secretion of proteins by recombinant host cells, it is possible to employ these recombinant host cells in a fermentation system which enables efficient production of a desired protein or polypeptide that can be purified at high yield and at minimal expense compared to existing fermentation/purification procedures. Moreover, the constructs of the present invention can be employed to bioprospect for potential effector proteins or polypeptides, which by virtue of their expression and secretion by a recombinant host cell expressing a type III secretion system, become likely candidates as effector proteins. This method of screening for potential effector protein is novel and much more systematic and efficient than prior methods.

MPMI 11(6):563–567 (1998); Bogdanove et al., "*Erwinia amylovora* Secretes Harpin via a Type III of Pathway and Contains a Homolog of YopN of Yersinia spp.," *J. Bacteriol.* 178:1720–1730 (1996); Wei et al., "Harpin, Elicitor of the Hypersensitive Response Produced by the Plant Pathogen *Erwinia amylovora,*" *Science*, 257:85–88 (1992); Wei et al., "HrpI of *Erwinia amylovora* Functions in Secretion of Harpin and is a Member of a New Protein Family," *J. Bacteriol.*, 175:7958–7967 (1993); Kim et al., "The HrpA and HrpC Operons of *Erwinia amylovora* Encode Components of a Type III Pathway that Secrets Harpin," *J. Bacteriol.* 179:1690–1697 (1997), which are hereby incorporated by reference). Arrow-shaped boxes denote putative transcriptional units. Shadowed areas denote hrp regions. Dashed boxes denote transcriptional units predicted on the basis of the homology and spacing of partially sequenced regions (shaded areas) in comparison with the corresponding *Erwinia amylovora* hrp genes. The filled triangle indicates the location of mini-Tn5Cm in pCPP2368.

Figure 2:
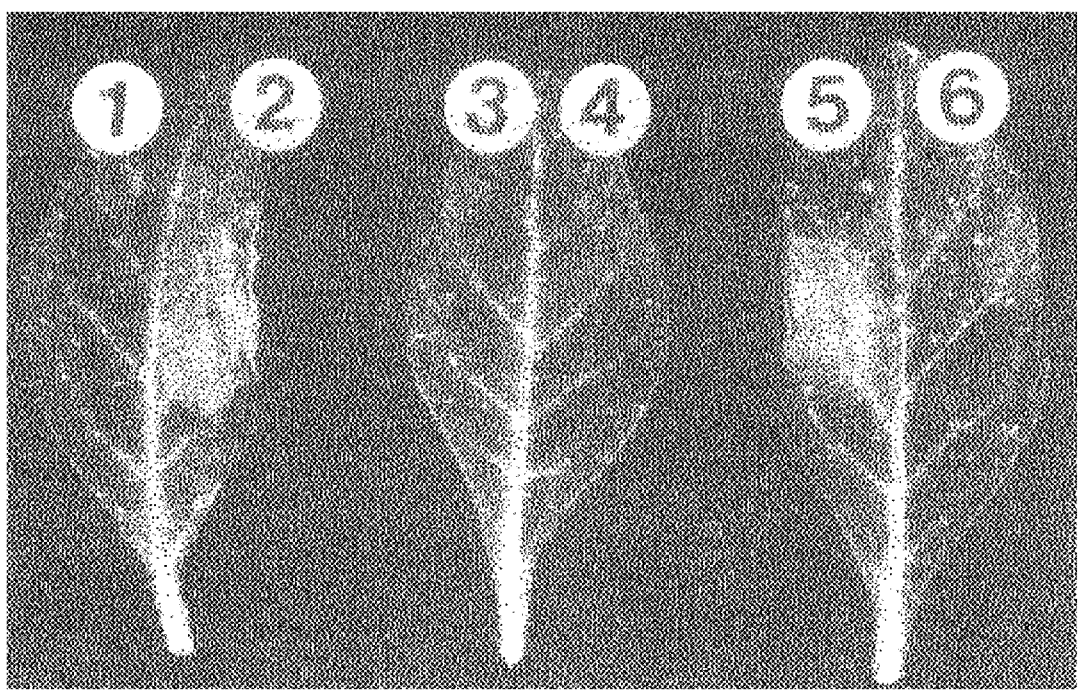

FIG. 2 contains images of *Nicotiana clevelandii* leaves infiltrated with *Escherichia coli* DH5α carrying *Erwinia chrysanthemi* hrp clusters that are either intact (pCPP2156, pCPP2416) or defective (pCPP2157, pCPP2368) at a concentration of 5×10$^8$ cfu/ml. Leaves were photographed 48 hours after infiltration. Tissue collapse occurred within 24 hours. The areas below each number on the leaf was infiltrated with *Escherichia coli* DH5α carrying following constructs: 1, pCPP2156; 2, pCPP2156 and pAVRB-FLAG2; 3, pCPP2157; 4, PCPP2157 and pAVRB-FLAG2; 5, pCPP2416 and pAVRB-FLAG2; 6, pCPP2368 and pAVRB-FLAG2.

Figure 3:
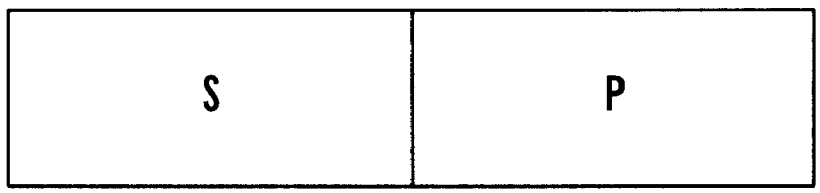
Figure 3:
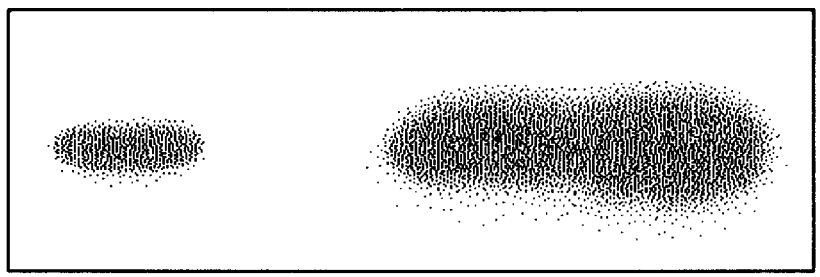

FIG. 3 is an image of an immunodetection in western blots showing differential secretion of AvrB-FLAG by *Escherichia coli* DH5α carrying either a wild type (pCPP2156) or mutant (pCPP2368) *Erwinia chrysanthemi* hrp cluster. The supernatant fraction (S) was concentrated 7.5× more than the cell pellet fraction (P). Lanes: 1, *Escherichia coli*(pCPP2156), pAVRB-FLAG2); 2, *Escherichia coli* (pCPP2368, pAVRB-FLAG2); 3, *Escherichia coli* (pCPP2156, pAVRB-FLAG2); 4, *Escherichia coli* (pCPP2368), pAVRB-FLAG2).

Figure 4:
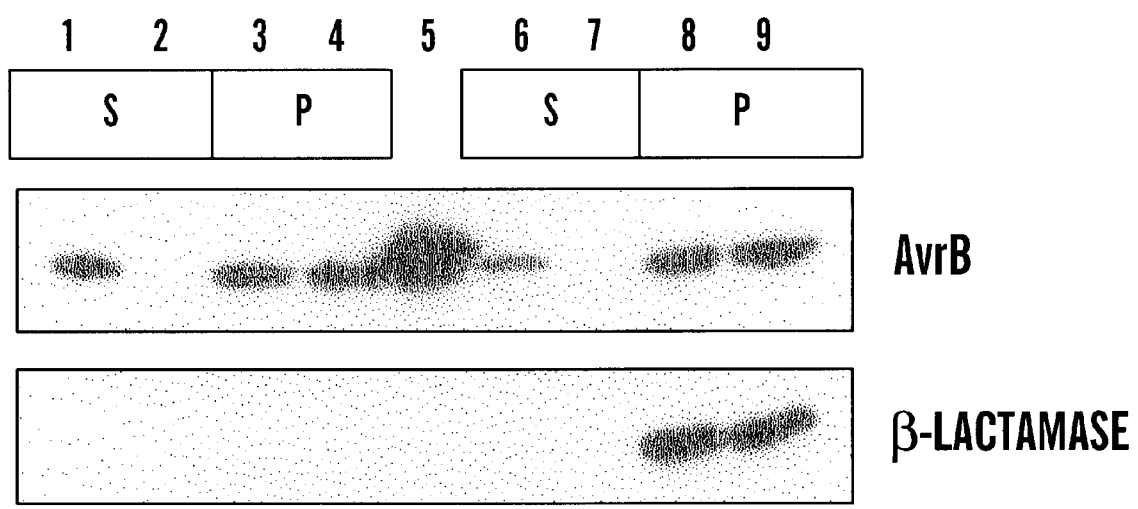

FIG. 4 is an image of an immunodetection in western blots showing differential secretion of AvrB by *Escherichia coli* DH5α carrying either a wild type (pCPP2156) or mutant (pCPP2368) *Erwinia chrysanthemi* hrp cluster. pCPP2138 encodes mature β-lactamase, which was used as a cytoplasmic marker. The supernatant fraction (S) was concentrated 7.5× more than the cell pellet fraction (P) for lanes 1 and 2 and 15× more for lanes 6 and 7. Lanes: 1, *Escherichia coli*(pCPP2156, pAVRB1); 2, *Escherichia coli*(pCPP2368, pAVRB1); 3, *Escherichia coli*(pCPP2156, pAVRB1); 4, *Escherichia coli*(pCPP2368), pAVRB1); 5, purified AvrB; 6, *Escherichia coli*(pCPP2156, pAVRB 1, pCPP2318); 7, *Escherichia coli*(pCPP2368, pAVRB 1, pCPP2318); 8 *Escherichia coli*(pCPP2156, pAVRB 1, pCPP2318); 9, *Escherichia coli*(pCPP2368, pAVRB 1, pCRPP2318).

Figure 5:
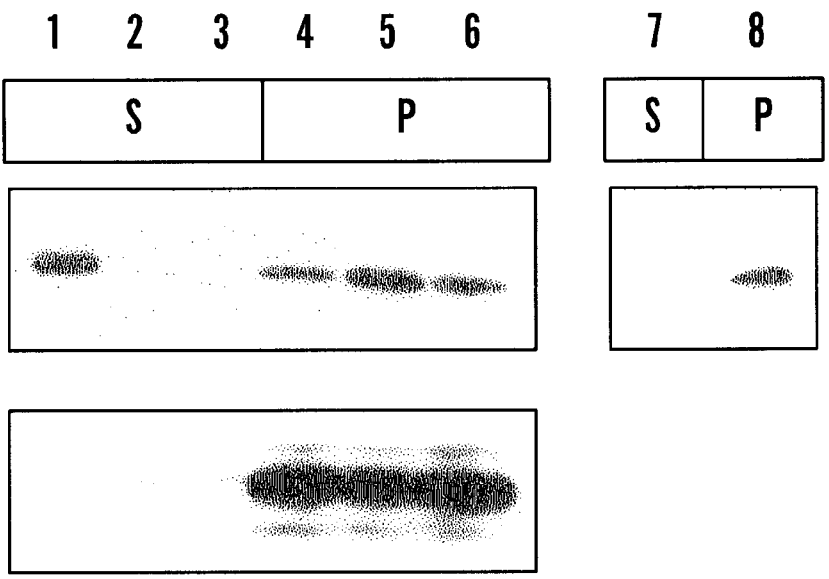

FIG. 5 is an image of an immunodetection in western blots showing differential secretion of AvrPto-FLAG by *Escherichia coli* DH5α carrying either intact (pCPP2156) or defective (pCPP2157, pCPP2368) *Erwinia chrysanthemi* hrp clusters and *Escherichia coli* MC4100 carrying pHIR11. As indicated above, pCPP2138 encodes mature β-lactamase, which was used as a cytoplasmic marker. The supernatant fraction (S) was concentrated 7.5× more than the cell pellet fraction (P). Lanes: 1, *Escherichia coli*(pCPP2156), pCPP2318, pAVRPTO-FLAG); 2, *Escherichia coli* (pCPP2157, pCPP2318, pAVRPTO-FLAG); 3, *Escherichia coli*(pCPP2368, pCPP2318, pAVRPTO-FLAG); 4, *Escherichia coli*(pCPP2156, pCPP2318, pAVRPTO-FLAG); 5, *Escherichia coli*(pCPP2157, pCPP2318, pAVRPTO-FLAG); 6, *Escherichia coli*(pCPP2368, pCPP2318, pAVRPTO-FLAG); 7, *Escherichia coli*(pHIR11, pAVRPTO-FLAG); 8, *Escherichia coli*(pHIR11, pAVRPTO-FLAG).

FIG. 6 is an image of the immunodetection of DspE and DspEÆ1521 in western blots of culture supernatant and bacterial cell fractions using anti-DspE antiserum (see Bogdanove et al., *J. Bacteriol.* 180:2244–2247 (1998), which is hereby incorporated by reference). Lane 1, hrp mutant Ea273-K178; lane 2, wild-type strain Ea273; lane 3, partial dspE deletion mutant Ea273dspEÆ1521. The migration of the molecular weight markers (BRL) is indicated at the left.

Figure 7:
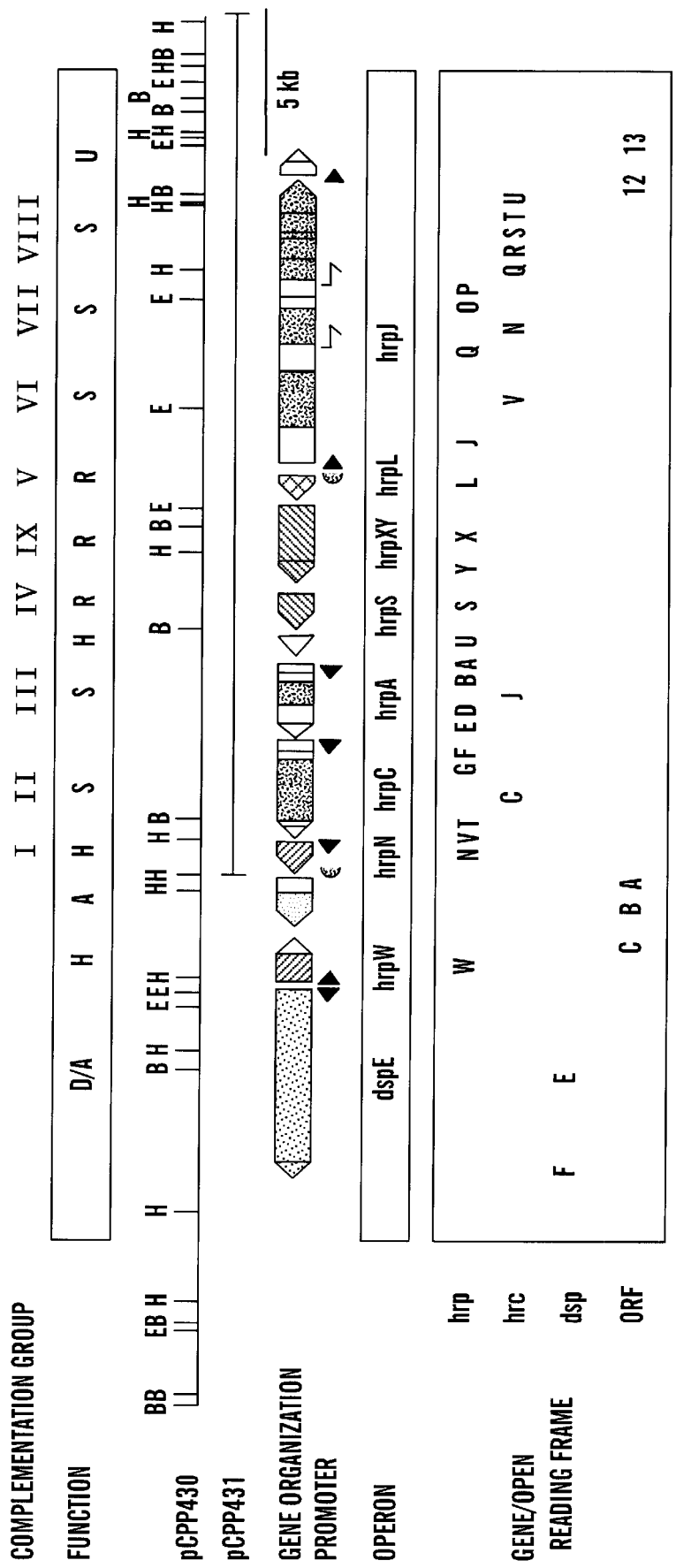

FIG. 7 is a diagram showing the genetic organization of the hrp and dsp genes contained by cosmids pCPP430 and pCPP431. The letters designating the known or proposed functions correspond to the following: S, secretion; R, regulation; H, harpin; A, avirulence; D, disease; U, unknown.

Figure 8:
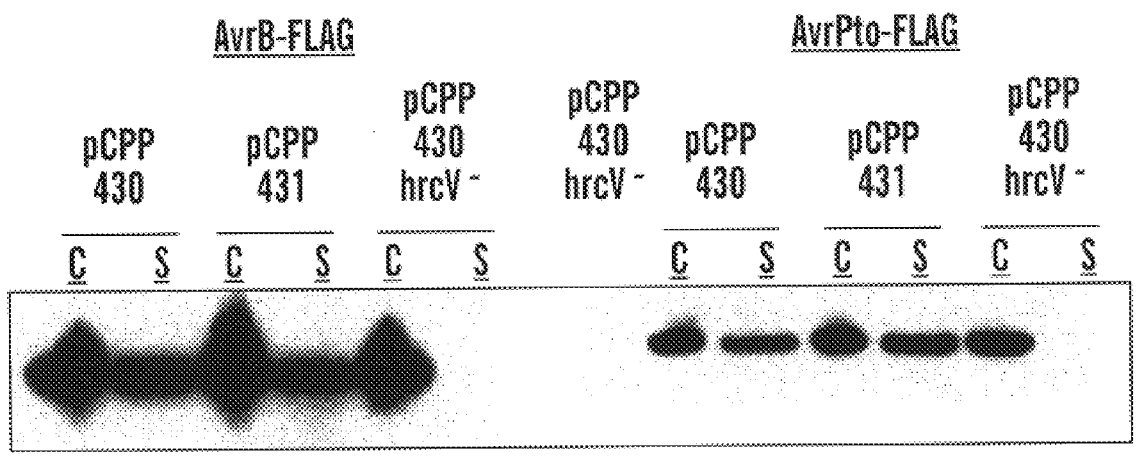

FIG. 8 is an image of an immunodetection in western blots of flagged *Pseudomonas syringae* Avr proteins in cell (C) and supernatant (S) fractions from cultures of *Escherichia coli* DH5 containing the designated Avr protein (AvrB-Flag or AvrPto-Flag) and the hrp/dsp cluster (pCPP430), the minimal hrp cluster (pCPP431), or the secretion-defective hrp cluster (pCPP430hrcVÐ).

DETAILED DESCRIPTION OF THE INVENTION

One aspect of the present invention relates to novel constructs that can be used to transform host cells so that they express and secrete (i.e., into the host cell environment) a protein or polypeptide of interest.

According to one embodiment, a DNA construct is provided which includes a first DNA molecule encoding a functional type III secretion system, a promoter, and a second DNA molecule encoding a protein or polypeptide capable of being secreted by the type III secretion system. The second DNA molecule is operably coupled to the promoter so that upon introduction of the DNA construct into a host cell, the encoded protein or polypeptide and the type III secretion system are expressed and the encoded protein or polypeptide is secreted by the host cell.

According to a second embodiment, a pair of DNA constructs are utilized as part of a system. The first DNA construct includes a DNA molecule encoding a functional type III secretion system. The second DNA construct includes a promoter operably coupled to a DNA molecule encoding a protein or polypeptide capable of being secreted by the type III secretion system. Upon introduction of the first and second DNA constructs into a host cell, the protein or polypeptide and the type III secretion system are expressed and the protein or polypeptide is secreted.

As used in each of the above embodiments, any functional type III secretion system can be employed. By functional, it is intended that the type III secretion system contain all required genes under appropriate transcriptional and/or translational control such that the secretion system can secrete proteins or polypeptides that are capable of being secreted. Preferred type III secretion systems are those obtained from the genus Erwinia, more preferably the harpin secretion systems obtained from *Erwinia amylovora* or

Figure 1:
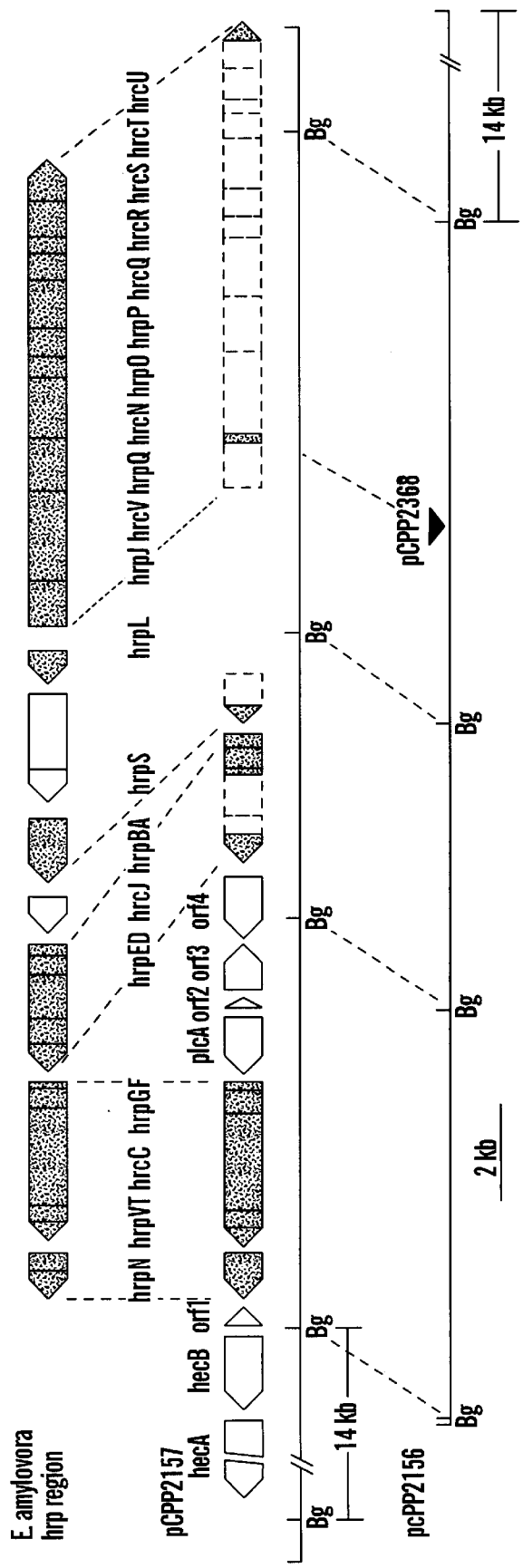
FIG. 1 is a diagram of the physical maps for cosmids pCPP2156 and pCPP2157, which contain the *Erwinia chrysanthemi* hrp region, and comparison of the hrp regions of *Erwinia chrysanthemi* and *Erwinia amylovora* (Bauer et al., "*Erwinia chrysanthemi* harpin$_{Ech}$: An Elicitor of the Hypersensitive Response that Contributes to Soft-rot Pathogenesis," *MPMI* 8:484–491 (1995); Kim et al., "The hrpC and hrpN Operons of *Erwinia chrysanthemi* EC16 are Flanked by plcA and Homologs of Hemolysin/Adhesin Genes and Accompanying Activator/Transporter Genes,"

*Erwinia chrysanthemi*, and Pseudomonas, more preferably the harpin secretion systems obtained from *Pseudomonas syringae*. For example, the harpin secretion system of *Erwinia amylovora* is present on cosmid pCPP430 (Beer et al., "The hrp Gene Cluster of *Erwinia amylovora*," in *Advances in Molecular Genetics of Plant-Microbe Interactions*, Proceedings of the 5th International Symposium on the Molecular Genetics of Plant-Microbe Interactions, Interlaken, Switzerland, September, 1990, pp. 53–60 (1991) which is hereby incorporated by reference) and the harpin secretion system of Erwinia carotovora is present in cosmid pCPP2156 (Ham et al., "A Cloned *Erwinia chrysanthemi* Hrp (type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA*, 95(17): 10206–11 (1998), which is hereby incorporated by reference). A diagram of cosmid pCPP430 is shown at FIG. 7 and a diagram of cosmid pCPP2156 is shown at FIG. 1.

Type III protein secretion systems are present in bacterial pathogens of both animals and plants, and are typified by the type III system of Yersinia spp. (Finlay et al., "Common Themes in Microbial Pathogenicity Revisited," *Microbiol. Mol. Biol. Rev.*, 61:136–169 (1997); Cornelis et al., "The Yersinia Yop Regulon: A Bacterial System for Subverting Eukaryotic Cells," *Mol. Microbiol.*, 23:861–867 (1997), which are hereby incorporated by reference). These animal pathogens are primarily extracellular parasites, and their Yops (Yersinia outer proteins) are secreted and translocated directly into host cells in a contact-dependent manner (Cornelis et al., "The Yersinia Yop Regulon: A Bacterial System for Subverting Eukaryotic Cells," *Mol. Microbiol.*, 23:861–867 (1997), which is hereby incorporated by reference). A similar host-contact dependency may operate in most plant pathogenic bacteria. Nine of the hrp genes are universal components of type III secretion systems, and these have been renamed hrc (HR and conserved) and given the last-letter designation of their Yersinia homolog (with the exception of hrck) (Bogdanove et al., "Unified Nomenclature for Broadly Conserved hrp Genes of Phytopathogenic Bacteria," *Mol. Microbiol.*, 20:681–683 (1996), which is hereby incorporated by reference). The Hrc proteins enable protein movement across the bacterial inner and outer membranes independently of the general protein export (Sec) pathway (Charkowski et al., "Altered Localization of HrpZ in *Pseudomonas syringae* pv. *syringae* hrp Mutants Suggests That Different Components of the Type III Secretion Pathway Control Protein Translocation Across the Inner and Outer Membranes of Gram-negative Bacteria," *J. Bacteriol.*, 179:3866–3874 (1997), which is hereby incorporated by reference). In contrast to the Hrc proteins, the Hrp proteins may be peripheral components of the Hrp secretion system and are more likely to perform type III secretion functions that are extracellular and specific to protein transfer across the plant cell wall and plasma membrane.

The genes encoding type III secretion systems are usually clustered, and the emerging concept that genes with related functions in virulence are often grouped on plasmids or in horizontally-acquired pathogenicity islands has important implications throughout pathogenic microbiology (Lawrence et al., "Selfish Operons: Horizontal Transfer May Drive the Evolution of Gene Clusters," *Genetics*, 143:1843–1860 (1996); Groisman et al., "Pathogenicity Islands: Bacterial Evolution in Quantum Leaps," *Cell*, 87:791–794 (1996); Hacker et al., "Pathogenicity Islands of Virulent Bacteria: Structure, Function and Impact on Microbial Evolution," *Mol. Microbiol.*, 23:1089–1097 (1997), which are hereby incorporated by reference). There is some evidence for horizontal acquisition of hrp gene clusters in plant pathogenic bacteria, and the hrp cluster in *Ralstonia solanacearum* is carried on a megaplasmid (Alfano et al., "Bacterial Pathogens in Plants: Life Up Against the Wall," *Plant Cell*, 8:1683–1698 (1996), which is hereby incorporated by reference). The finding of a plasmid-borne hrp gene cluster in *Erwinia herbicola* pv. *gypsophilae* suggests that virulence may be acquired readily by plant-associated bacteria (Nizan et al., "The Presence of hrp Genes on the Pathogenicity-associated Plasmid of the Tumorigenic Bacterium *Erwinia herbicola* pv. *gypsophilae*," *MPMI*, 10:677–682 (1997), which is hereby incorporated by reference). *Erwinia herbicola* is a common epiphyte that is usually benign, but strains classified as *Erwinia herbicola* pv. *gypsophilae* cause galls on gypsophila and elicit the HR in tobacco. A 150-kb plasmid carries phytohormone biosynthetic genes and hrp genes, and the latter are required both for gall formation and HR elicitation (Nizan et al., "The presence of hrp genes on the pathogenicity-associated Plasmid of the Tumorigenic Bacterium *Erwinia herbicola* pv. *gypsophilae*," *MPMI*, 10:677–682 (1997), which is hereby incorporated by reference).

The clustering of genes with related function is also consistent with the ability of some cloned hrp clusters to enable nonpathogens like *Escherichia coli* to elicit the HR. This has been reported for cosmids pHIR11 from *Pseudomonas syringae* pv. syringae, pCPP430 from *Erwinia amylovora*, pPPY430 from *Pseudomonas syringae* pv. *phaseolicola*, and pCPP2156 from *Erwinia chrysanthemi* (Alfano et al., "Bacterial Pathogens in Plants: Life Up Against the Wall," *Plant Cell*, 8:1683–1698 (1996); Puri et al., "Expression of avrPphB, an Avirulence Gene from *Pseudomonas syringae* pv. *phaseolicola*, and the Delivery of Signals Causing the Hypersensitive Reaction in Bean," *MPMI*, 10:247–256 (1997); Ham et al., "A Cloned *Erwinia chrysanthemi* Hrp (type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA*, 95(17): 10206–11 (1998), which are hereby incorporated by reference). Although these cosmids support heterologous HR elicitation, they do not enable *Escherichia coli* to become pathogenic. The basis for HR elicitation is best understood with pHIR11. The cosmid carries a 25-kb set of hrp genes that is intact and functional, as revealed by DNA sequencing and the ability to direct secretion of the HrpZ harpin (Alfano et al., "The Type III (Hrp) Secretion Pathway of Plant Pathogenic Bacteria: Trafficking Harpins, Avr Proteins, and Death," *J. Bacteriol.* 179:5655–5662 (1997), which is hereby incorporated by reference). The cosmid also carries, adjacent to the hrp cluster, the hrmA gene, which is avr-like in producing an avirulence phenotype when expressed in a tobacco pathogen and in being lethal when heterologously expressed inside nonhost tobacco cells (Alfano et al., "Evidence That the *Pseudomonas syringae* pv. *syringae* hrp-linked hrmA Gene Encodes an Avr-like Protein that Acts in a hrp-dependent Manner Within Tobacco Cells," *MPMI*, 10:580–588 (1997), which is hereby incorporated by reference). The concept that the minimal requirement for bacterial elicitation of the HR is a functional Hrp system and an avr gene whose product is recognized by the R-gene surveillance system of the test plant is supported by experiments in which the HR is observed only when an appropriate, heterologous avr gene is supplied in trans of the hrp$^+$ cosmid (Puri et al., "Expression of avrPphB, an Avirulence Gene from *Pseudomonas syringae* pv. *phaseolicola*, and the Delivery of Signals Causing the Hypersensitive Reaction in Bean," *MPMI,* 10:247–256 (1997); Ham et al., "A Cloned *Erwinia chrysanthemi* Hrp (type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA,* 95(17): 10206–11 (1998); Gopalan, S. et al., "Expression of the *Pseudomonas syringae* Avirulence Protein AvrB in Plant Cells Alleviates its Dependence on the Hypersensitive Response and pathogenicity (Hrp) Secretion System in Eliciting Genotype-specific Hypersensitive Cell Death," *Plant Cell,* 8:1095–1105 (1996); Pirhonen et al., "Phenotypic Expression of *Pseudomonas syringae* avr Genes in *E. Coli* is Linked to the Activities of the hrp-encoded Secretion System," *MPMI* 9:252–260 (1996), which are hereby incorporated by reference).

hrp genes are expressed in plants and in apoplast-mimicking minimal media, but typically not in complex media (Lindgren, "The Role of hrp Genes During Plant-Bacterial Interactions," *Annu. Rev. Phytopathol,* 35:129–152 (1997), which is hereby incorporated by reference). The Hrp regulatory systems in plant pathogenic bacteria can be divided into two groups, which correspond also to differences in hrp cluster composition (Alfano et al., "The Type III (Hrp) Secretion Pathway of Plant Pathogenic Bacteria: Trafficking Harpins, Avr Proteins, and Death," *J. Bacteriol.* 179:5655–5662 (1997), which is hereby incorporated by reference). In the group I Hrp systems of Erwinia and Pseudomonas, hrp operons are activated by HrpL, an alternate sigma factor (Lindgren, "The Role of hrp Genes During Plant-Bacterial Interactions," *Annu. Rev. Phytopathol.* 35:129–152 (1997); Hutcheson, "The hrp-encoded Protein Export Systems of *Pseudomonas syringae* and Other Plant Pathogenic Bacteria and Their Role in Pathogenicity," in *Plant-Microbe Interactions Volume* 3, ed. Stacey and Keen, New York: Chapman and Hall, Inc., pp. 145–179 (1997), which are hereby incorporated by reference). In contrast, hrp transcription is activated by an AraC homolog in the group II Hrp systems of Xanthomonas (HrpX) and Ralstonia (HrpB) (Lindgren, "The Role of hrp Genes During Plant-Bacterial Interactions," *Annu. Rev. Phytopathol.* 35:129–152 (1997), which is hereby incorporated by reference). Upstream activators of these factors have been described for *Pseudomonas syringae* (HrpR and HrpS, $\Phi^{54}$-dependent promoter enhancer-binding protein homologs) (Lindgren, "The Role of hrp Genes During Plant-Bacterial Interactions", *Annu. Rev. Phytopathol,* 35:129–152 (1997); Hutcheson, "The hrp-encoded Protein Export Systems of *Pseudomonas syringae* and Other Plant Pathogenic Bacteria and Their Role in Pathogenicity," in *Plant-Microbe Interactions, Volume* 3, ed. Stacey and Keen, New York: Chapman and Hall, Inc., pp. 145–179 (1997), which are hereby incorporated by reference), *Xanthomonas campestris* pv. *vesicatoria* (HrpG, OmpR homolog) (Wengelnik et al., "HrpG, a Key hrp Regulatory Protein of *Xanthomonas campestris* pv. *vesicatoria* is Homologous to Two-component Response Regulators," *MPMI* 9:704–712 (1996), which is hereby incorporated by reference), and *R. solanacearum* (PrhA) (Marenda et al., "PrhA Controls a Novel Regulatory Pathway Required for the Specific Induction of *Ralstonia solanacearum* hrp Genes in the Presence of Plant Cells," *Mol. Microbiol.* 27:437–453 (1998), which is hereby incorporated by reference). The recent discovery of PrhA is particularly significant because this homolog of TonB-dependent outer membrane siderophore receptors, which appears to act at the top of the Hrp regulatory hierarchy, is required specifically for induction of hrp genes in the presence of plant cells and for full virulence in Arabidopsis (Marenda et al., "PrhA Controls a Novel Regulatory Pathway Required for the Specific Induction of *Ralstonia solanacearum* hrp Genes in the Presence of Plant Cells," *Mol. Microbiol.* 27:437–453 (1998), which is hereby incorporated by reference). In the host-promiscuous pathogen *Erwinia carotovora,* production of the hrpN-encoded harpin is activated by the quorum sensing signal, N-(3-oxohexanoyl)-L-homoserine lactone and negatively regulated by RsmA, two global regulators similarly controlling exoenzyme production (Mukherjee et al., "Molecular Characterization and Expression of the *Erwinia carotovora* hrp-$N_{Ecc}$ gene, Which Encodes An Elicitor of the Hypersensitive Reaction," *MPMI* 10:462–471 (1997); Cui, Y. et al., "The $RsmA^-$ Mutants of *Erwinia carotovora* subsp. *carotovora* Strain Ecc71 Overexpress hrp$N_{Ecc}$ and Elicit a Hypersensitive Reaction-like Response in Tobacco Leaves," *MPMI,* 9–6565–573 (1996), which are hereby incorporated by reference).

The protein or polypeptide must be compatible for secretion by the type III secretion system employed. By compatible, it is intended that the protein or polypeptide contain a secretion signal that can be recognized by the particular type III secretion system that is employed. The secretion signal enables the expressed protein or polypeptide to be recognized by the type III secretion system and transported via the expressed secretion system into the extracellular environment in which the recombinant host cells exist, i.e., culture medium.

Suitable secretion signals can be either an mRNA or a polypeptide fragment of a naturally-occurring protein secreted by the type III secretion system.

Compatible secretion signals can readily be determined for any particular type III secretion system that is to be employed. By identifying proteins that are normally secreted by the type III secretion system, it is possible to prepare deletion mutants missing various fragments of the full length protein that is normally secreted by the secretion system. Using labeled antibodies raised against epitopes of the various deletion fragments that are expressed (i.e., N-terminal epitopes, C-terminal epitopes, etc.), it is possible to identify deletion mutants that are secreted and those that are not secreted. Thus, protein domains necessary for secretion of the full length protein can be readily identified. Once the protein domains have been identified and sequenced, they can be utilized as secretion signals in fusion proteins of the present invention.

Typically, the secretion signal is an N-terminal domain of a protein that is normally secreted by the particular type III secretion system. An exemplary secretion signal is a 201 amino acid sequence from the N-terminal domain of the DspE protein of *Erwinia amylovora*, which has an amino acid sequence corresponding to SEQ. ID. No. 1 as follows:

```
Met Glu Leu Lys Ser Leu Gly Thr Glu His Lys Ala Ala Val His Thr
1               5                   10                  15

Ala Ala His Asn Pro Val Gly His Gly Val Ala Leu Gln Gln Gly Ser
                20                  25                  30

Ser Ser Ser Ser Pro Gln Asn Ala Ala Ala Ser Leu Ala Ala Glu Gly
            35                  40                  45

Lys Asn Arg Gly Lys Met Pro Arg Ile His Gln Pro Ser Thr Ala Ala
        50                  55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
            115                 120                 125

Arg Leu Thr Arg Ser Gly Gly Val Lys Arg Arg Asn Met Asp Asp Met
        130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile
        195                 200
```

This amino acid sequence is encoded by a DNA molecule having a 603 base nucleic acid sequence from the gene or gene fragment coding for DspE. This DNA molecule has a nucleotide sequence corresponding to SEQ. ID. No. 2 as follows:

```
ATGGAATTAA AATCACTGGG AACTGAACAC AAGGCGGCAG TACACACAGC GGCGCACAAC   60

CCTGTGGGGC ATGGTGTTGC CTTACAGCAG GGCAGCAGCA GCAGCAGCCC GCAAAATGCC  120

GCTGCATCAT TGGCGGCAGA AGGCAAAAAT CGTGGGAAAA TGCCGAGAAT TCACCAGCCA  180

TCTACTGCGG CTGATGGTAT CAGCGCTGCT CACCAGCAAA AGAAATCCTT CAGTCTCAGG  240

GGCTGTTTGG GGACGAAAAA ATTTTCCAGA TCGGCACCGC AGGGCCAGCC AGGTACCACC  300

CACAGCAAAG GGGCAACATT GCGCGATCTG CTGGCGCGGG ACGACGGCGA AACGCAGCAT  360

GAGGCGGCCG CGCCAGATGC GGCGCGTTTG ACCCGTTCGG GCGGCGTCAA ACGCCGCAAT  420

ATGGACGACA TGGCCGGGCG GCCAATGGTG AAAGGTGGCA GCGGCGAAGA TAAGGTACCA  480

ACGCAGCAAA AACGGCATCA GCTGAACAAT TTTGGCCAGA TGCGCCAAAC GATGTTGAGC  540

AAAATGGCTC ACCCGGCTTC AGCCAACGCC GGCGATCGCC TGCAGCATTC ACCGCCGCAC  600

ATC                                                                603
```

The 201 amino acid secretion signal of *Erwinia amylovora* DspE is compatible with the harpin secretion system of *Erwinia amylovora*. Other secretion signals that are compatible with various type III secretion systems have been described in the art and other are continually being identified.

Human-pathogenic Yersinia spp. use the type III secretion system to deliver seven effector Yops into the host cytoplasm and another three Yops to the bacterial milieu (Hueck, "Type III Protein Secretion Systems in Bacterial Pathogens of Animals and Plants," *Microbiol. Mol. Biol. Rev.* 62:379–433 (1998), which is hereby incorporated by reference). All Yops carry an mRNA targeting signal in their first 15 codons (Anderson and Schneewind, "A mRNA Signal for the Type III Secretion of Yop Proteins by *Yersinia enterocolitica,*" *Science* 278:1140–1143 (1997); Anderson and Schneewind, "Type III Machines of Gram-negative Pathogens: Injecting Virulence Factors into Host Cells and More," *Curr. Opin. Microbiol.* 2:18–24 (1999), which are hereby incorporated by reference). Fusion of the first 15 codons of YopE to an Npt reporter is sufficient for type III secretion of the hybrid to the bacterial milieu, and mutations shifting the reading frame of these codons do not abolish secretion (Anderson and Schneewind, "A mRNA Signal for the Type III Secretion of Yop Proteins by *Yersinia enterocolitica*", *Science* 278:1140–1143 (1997), which is hereby incorporated by reference). Thus, the targeting information resides in the mRNA rather than the encoded peptide. The mRNA targeting signal appears universal among effector proteins secreted by the type III pathways of animal pathogens and plant pathogens. For example, *Yersinia enterocolitica* strongly secretes AvrB and AvrPto, and *Escherichia coli* (pCPP2156) secretes (much less efficiently) YopE and YopQ (Anderson et al., "mRNA Signal Universal to Plant and Animal Pathogens," *Proc. Natl. Acad. Sci. USA* (1999), which is hereby incorporated by reference). The first 15 codons of avrB and avrPto are necessary for secretion from *Escherichia coli*(pCPP2156), and they are sufficient to target an AvrPto$_{1-15}$-Npt hybrid for secretion in Yersinia and *Pseudomonas syringae* (Anderson et al., "mRNA Signal Universal to Plant and Animal Pathogens," *Proc. Natl. Acad. Sci. USA* (1999), which is hereby incorporated by reference). Frame-shift mutations changing the peptide encoded by the AvrPto$_{1-15}$ mRNA do not prevent secretion of Npt in Yersinia (Anderson et al., "mRNA Signal Universal to Plant and Animal Pathogens," *Proc. Natl. Acad. Sci. USA* (1999), which is hereby incorporated by reference). Thus, the mRNA signal recognized by type III secretion systems appears to be universal.

The protein or polypeptide can be a naturally secreted protein or polypeptide homologous to the type III secretion system (i.e., normally secreted by the source organism from which the type III secretion system was obtained) or heterologous to the type III secretion system (i.e., normally secreted by a source organism other than that from which the type III secretion system was obtained). By way of example, a naturally secreted protein or polypeptide homologous to the harpin secretion systems of *Erwinia amylovora* include, among others, DspE and HrpN. Exemplary naturally secreted proteins or polypeptides which are heterologous to the harpin secretion systems of Erwinia include the various *Pseudomonas syringae* Avr proteins.

Two classes of extracellular Hrp proteins have now been defined—harpins and pilins. Harpins are glycine-rich proteins that lack cysteine, are secreted in culture when the Hrp systems is expressed, and possess heat-stable HR elicitor activity when infiltrated into the leaves of tobacco and several other plants (Alfano et al., "Bacterial Pathogens in Plants: Life Up Against the Wall," *Plant Cell,* 8:1683–1698 (1996), which is hereby incorporated by reference). Mutation of the prototypical hrpN harpin gene in *Erwinia amylovora* Ea321 strongly diminishes HR and pathogenicity phenotypes (Kim et al., "HrpW of *Erwinia amylovora,* a New Harpin That is a Member of a Proposed Class of Pectate Lyases," *J. Bacteriol.* 180(19):5203–5210 (1998), which is hereby incorporated by reference), but mutation of the hrpZ harpin gene in different *Pseudomonas syringae* strains has little or no effect on Hrp phenotypes (Alfano et al., "Analysis of the Role of the *Pseudomonas syringae* pv. *syringae* HrpZ Harpin in Elicitation of the Hypersensitive Response in Tobacco Using Functionally Nonpolar Deletion Mutations, Truncated HrpZ Fragments, and hrmA Mutations," *Mol. Microbiol.* 19:715–728 (1996); Charkowski et al., "The *Pseudomonas syringae* pv. *tomato* HrpW Protein Has Domains Similar to Harpins and Pectate Lyases and Can Elicit the Plant Hypersensitive Response and Bind to Pectate," *J. Bacteriol.* 180 (19):5211–5217 (1998), which are hereby incorporated by reference). The natural function of harpins or the basis for their ability to elicit an apparent programmed cell death when artificially introduced into the apoplast of plants is unknown. However, two lines of evidence point to a site of action in the plant cell wall. First, purified *Pseudomonas syringae* harpin binds to cell walls and has biological activity only with walled cells (Hoyos et al., "The Interaction of Harpin$_{Pss}$ With Plant Cell Walls," *MPMI* 9:608–616 (1996), which is hereby incorporated by reference). Second, HrpW, a second harpin discovered in both *Erwinia amylovora* and *Pseudomonas syringae,* has an N-terminal half that is harpin-like but a C-terminal half that is homologous to a newly-defined class of pectate lyases found in fungal and bacterial pathogens (Kim et al., "HrpW of *Erwinia amylovora,* a New Harpin That is a Member of a Proposed Class of Pectate Lyases," *J. Bacteriol.* 180(19):5203–5210 (1998); Charkowski et al., "The *Pseudomonas syringae* pv. *tomato* HrpW Protein Has Domains Similar to Harpins and Pectate Lyases and Can Elicit the Plant Hypersensitive Response and Bind to Pectate," *J. Bacteriol.* 180 (19):5211–5217 (1998), which are hereby incorporated by reference). Elicitor activity resides in the harpin domain, and the pectate lyase domain, although lacking enzymatic activity, binds specifically to pectate (Charkowski, A. et al., "The *Pseudomonas syringae* pv. *tomato* HrpW Protein Has Domains Similar to Harpins and Pectate Lyases and Can Elicit the Plant Hypersensitive if. Response and Bind to Pectate," *J. Bacteriol.* 180 (19):5211–5217 (1998), which is hereby incorporated by reference). The second class of extracellular Hrp proteins are represented by the *Pseudomonas syringae* HrpA pilin, which is a subunit of a Hrp-pilus that is 6–8 nm in diameter and is formed on bacteria in a Hrp-dependent manner (Roine et al., "Hrp Pilus: An hrp-dependent Bacterial Surface Appendage Produced by *Pseudomonas syringae* pv. *tomato* DC3000," *Proc. Natl. Acad. Sci. USA* 94:3459–3464 (1997), which is hereby incorporated by reference). The Hrp pilus is required for pathogenicity and elicitation of the HR, and a similar structure is important for T-DNA transfer in *Agrobacterium tumefaciens* (Fullner et al., "Pilus Assembly by Agrobacterium T-DNA Transfer Genes," *Science,* 237:1107–1109 (1996), which is hereby incorporated by reference). Whether these structures promote the transfer of bacterial macromolecules into plant cells by serving as conduits, guides, or attachment factors is not known.

A current model for plant-bacterium interaction and co-evolution based on Hrp delivery of Avr proteins into plant cells proposes that (i) Avr-like proteins are the primary effectors of parasitism, (ii) conserved Hrp systems are capable of delivering many, diverse Avr-like proteins into plant cells, and (iii) genetic changes in host populations that reduce the parasitic benefit of an effector protein or allow its recognition by the R-gene surveillance system will lead to a proliferation of complex arsenals of avr-like genes in co-evolving bacteria (Alfano et al., "Bacterial Pathogens in Plants: Life Up Against the Wall," *Plant Cell,* 8:1683–1698 (1996), which is hereby incorporated by reference). There are still many gaps in this model. For example, the physical transfer of Avr proteins into plant cells has never been observed, the virulence functions of Avr proteins are unknown, and it is likely that previous searches for avr genes in various bacteria have yielded incomplete inventories of the genes in various bacteria and, thus, incomplete inventories of the genes encoding effector proteins.

Avr proteins have not been reported outside of the cytoplasm of living *Pseudomonas syringae* and Xanthomonas spp. cells (Leach et al., "Bacterial Avirulence Genes,"*Annul. Rev. Phytopathol,* 34:153–179 (1996); Puri et al., "Expression of avrPphB, an Avirulence Gene from *Pseudomonas Syringae* pv. *phaseolicola*, and the Delivery of Signals Causing the Hypersensitive Reaction in Bean," *MPMI* 10:247–256 (1997), which are hereby incorporated by reference), but it now appears that the Hrp systems of Erwinia spp. can secrete Avr proteins in culture. A homolog of the *Pseudomonas syringae* pv. *tomato* avrE gene has been found in *Erwinia amylovora* and designated dspA in strain CFBP1430 and dspE in strain Ea321 (Gaudriault et al., "DspA, an Essential Pathogenicity Factor of *Erwinia amylovora* Showing Homology with AvrE of *Pseudomonas syringae*, is Secreted via the Hrp Secretion Pathway in a DspB-dependent Way," *Mol. Microbiol.*, 26:1057–1069 (1997); Bogdanove et al., "Homology and Functional Similarity of a hrp-linked Pathogenicity Operon, dspEF, of *Erwinia amylovora* and the avrE locus of *Pseudomonas syringae* Pathovar Tomato," *Proc. Natl. Acad. Sci. USA*, 95:1325–1330 (1998), which are hereby incorporated by reference). dsp genes are required for the pathogenicity of *Erwinia amylovora*, but not for HR elicitation. A protein of the expected size of DspA is secreted in a Hrp- and DspB-dependent manner by CFBP1430 (DspB is a potential chaperone) (Gaudriault et al., "DspA, an Essential Pathogenicity Factor of *Erwinia amylovora* Showing Homology with AvrE of *Pseudomonas syringae*, is Secreted via the Hrp Secretion Pathway in a DspB-dependent Way," *Mol. Microbiol.*, 26:1057–1069 (1997), which is hereby incorporated by reference). Specific antibodies were used to demonstrate unambiguously that DspE is efficiently secreted in a Hrp-dependent manner by strain Ea321 (Bogdanove et al., "*Erwinia amylovora* Secretes DspE, a Pathogenicity Factor and Functional AvrE Homolog, Through the Hrp (Type III Secretion) Pathway," *J. Bacteriol.*, 180(8):2244–2247 (1998), which is hereby incorporated by reference).

Nothing is known of the localization or expected site of action of AvrE. However, there is strong evidence that the site of action of the *Pseudomonas syringae* AvrB and AvrPto proteins is inside plant cells (see Bonas et al., "Recognition of Bacterial Avirulence Proteins Occurs Inside the Plant Cell: A General Phenomenon in Resistance to Bacterial Diseases?," *Plant J.* 12:1 (1997); Baker et al., "Recognition and Signaling in Plant-Microbe Interactions," *Science*, 276:726–733 (1997), which are hereby incorporated by reference), and both proteins have now been found to be secreted by an *Erwinia chrysanthemi* Hrp system functioning heterologously in *Escherichia coli* (Ham et al., "A Cloned *Erwinia chrysanthemi* Hrp (type III Protein Secretion) System Functions in *Escherichia coli* to Deliver *Pseudomonas syringae* Avr Signals to Plant Cells and to Secrete Avr Proteins in Culture," *Proc. Natl. Acad. Sci. USA*, 95(17): 10206–11 (1998), which is hereby incorporated by reference). This secretion is Hrp-dependent, and *Escherichia coli* cells carrying the *Erwinia chrysanthemi* hrp genes also elicit an avrB-dependent HR in appropriate test plants. A strong implication of this work is that *Erwinia chrysanthemi*, which is a host-promiscuous soft-rot pathogen, also carries avr-like genes. The ability of the cloned *Erwinia chrysanthemi* Hrp system to secrete *Pseudomonas syringae* Avr proteins should promote searches for additional avr-like genes by providing a phenotype that is independent of plant tests, and it will enable direct investigation of Avr targeting signals and secretion mechanisms. For example, chaperone-independent targeting information in two Yersinia Yop proteins has been shown to reside in the mRNA encoding the N-terminus of the protein (Anderson et al., "A mRNA Signal for the Type III Secretion of Yop Proteins by *Yersinia Enterocolitica*," *Science*, 278:1140–1143 (1997), which is hereby incorporated by reference). The involvement of similar signals in Avr secretion is suggested by the need for continued protein (but not mRNA) synthesis in planta for Avr signal delivery, which would be consistent with a co-translational secretion process (Puri et al., "Expression of avrPphB, an Avirulence Gene from *Pseudomonas syringae* pv. *phaseolicola*, and the Delivery of signals Causing the Hypersensitive Reaction in Bean," *MPMI*, 10:247–256 (1997), which is hereby incorporated by reference).

The biochemical activities or parasite-promoting functions of Avr proteins remain unclear, although several of those known make measurable contributions to virulence (Leach et al., "Bacterial Avirulence Genes," *Annul. Rev. Phytopathol*, 34:153–179 (1996), which are hereby incorporated by reference). Members of the AvrBs3 family in Xanthomonas spp. are targeted to the plant nucleus (Van den Ackerveken et al., "Bacterial Avirulence Proteins as Triggers of Plant Defense Resistance," *Trends Microbiol*, (1997); Gabriel, "Targeting of Protein Signals from Xanthomonas to the Plant Nucleus," *Trends Plant Sci.*, 2:204–206 (1997), which are hereby incorporated by reference), and some of these have been shown recently to redundantly encode watersoaking functions associated with circulence (Yang et al., "Watersoaking Function(s) of XcmH1005 are Redundantly Encoded by Members of the Xanthomonas avr/pth Gene Family," *MPMI*, 9:105–113 (1996), which is hereby incorporated by reference. AvrD (*Pseudomonas syringae* pv. *tomato*) directs the synthesis of syringolide elicitors of the HR (Leach et al., "Bacterial Avirulence Genes," *Annul. Rev. Phytopathol*, 34:153–179 (1996), which is hereby incorporated by reference); AvrBs2 (*Xanthomonas campestris* pv. *vesicatoria*) shows similarity to A. *tumefaciens* agrocinopine synthase (Swords et al., "Spontaneous and Induced Mutations in a Single Open Reading Frame Alters Both Virulence and Avirulence in *Xanthomonas campestris* pv. *vesicatoria* avrBs2," *J. Bacteriol.*, 4661–4669 (1996), which is hereby incorporated by reference); and AvrRxv (*Xanthomonas campestris* pv. *vesicatoria*) is a homolog of AvrA (*Salmonella typhimurium*) and YopJ (Yersinia spp.), proteins which travel the type III pathway in animal pathogens and trigger apoptosis in macrophages (Hardt et al., "A Secreted Salmonella Protein With Homology to an Avirulence Determinant of Plant Pathogenic Bacteria," *Proc. Natl. Acad. Sci. USA*, 94:9887–9892 (1997); Monack et al., Yersinia Signals Macrophages to Undergo Apoptosis and YopJ is Necessary for this Cell Death," *Proc. Natl. Acad. Sci. USA*, 94:10385–10390 (1997), which are hereby incorporated by reference. This last observation has led to the suggestion that avr-R gene interactions may occur also in animal pathogenesis (Galan, "'Avirulence Genes' in Animal Pathogens?," *Trends Microbiol.*, 6:3–6 (1998), which is hereby incorporated by reference.

The primary sequences of the *Pseudomonas syringae* Avr proteins reveal little about their potential function, but interestingly, when heterologously expressed in plants, three of them have produced necrosis in test plants lacking the cognate R gene (Gopalan et al., "Expression of the *Pseudomonas syringae* Avirulence Protein AvrB in Plant Cells Alleviates its Dependence on the Hypersensitive Response and pathogenicity (Hrp) Secretion System in Eliciting Genotype-specific Hypersensitive Cell Death," *Plant Cell,* 8:1095–1105 (1996); Stevens et al., "Sequence Variations in Alleles of the Avirulence Gene avrPphE R2 from *Pseudomonas syringae* pv. *phaseolicola* Lead to Loss of Recognition of the AvrPphE Protein Within Bean Cells and Gain in Cultivar Specific Virulence," *Mol. Microbiol.*, 29(1):165–77 (1998); McNellis et al., "Glucocorticoid-inducible Expression of a Bacterial Avirulence Gene in Transgenic Arabidopsis Induces Hypersensitive Cell Death," *Plant J.,* 14(2):247–57 (1998), which are hereby incorporated by reference). A key question is whether this results from interaction of abnormally high levels of the bacterial protein with plant virulence targets or with cross-reacting R-gene products. Further evidence suggesting that some avr genes in *Pseudomonas syringae* are beneficial to the bacteria in host plants is found in recent studies of avrD and avrPphE. Highly conserved, nonfunctional alleles of these genes have been retained in pathogens whose hosts would recognize the functional Avr product (Stevens et al., "Sequence Variations in Alleles of the Avirulence Gene avrPphE.R2 from *Pseudomonas syringae* pv. *phaseolicola* Lead to Loss of Recognition of the AvrPphE Protein Within Bean Cells and Gain in Cultivar Specific Virulence," *Mol. Microbiol.,* 29(l):165–77 (1998); Keith et al., "Comparison of avrD Alleles from *Pseudomonas syringae* pv. *glycinea," MPMI,* 10:416–422 (1997), which are hereby incorporated by reference).

Avr-like genes may function heterologously to support pathogenesis as well as HR elicitation. The pathogenicity of an *Erwinia amylovora* dspE mutant can be restored (at least partially) by a plasmid carrying the *Pseudomonas syringae* avrE locus, suggesting that DspE and AvrE have similar functions (Bogdanove et al., "Homology and Functional Similarity of a hrp-linked Pathogenicity Operon, dspEF, of *Erwinia amylovora* and the avrE locus of *Pseudomonas syringae* Pathovar *Tomato," Proc. Natl. Acad. Sci. USA,* 95:1325–1330 (1998), which is hereby incorporated by reference). That dspE is essential for *Erwinia amylovora* pathogenicity, whereas avrE contributes only quantitatively to the virulence of *Pseudomonas syringae* pv *tomato* (Lorang et al., "avrA and avrE in *Pseudomonas Syringae* pv. *Tomato* PT23 Play a Role in Virulence on Tomato Plants," *MPMI,* 7:508–515 (1994), which is hereby incorporated by reference), suggests that there is less redundancy in the *Erwinia amylovora* virulence system. This would be consistent with a more recent acquisition of the Hrp system by *Erwinia amylovora* and/or a slower coevolution with its perennial hosts (Bogdanove et al., "Homology and Functional Similarity of a hrp-linked Pathogenicity Operon, dspEF, of *Erwinia amylovora* and the avrE locus of *Pseudomonas syringae* Pathovar *Tomato," Proc. Natl. Acad. Sci. USA,* 95:1325–1330 (1998), which is hereby incorporated by reference). The heterologous function of *Pseudomonas syringae* avr genes in *Erwinia amylovora* and *Erwinia chrysanthemi* suggests that Hrp+ bacteria in the field may be able to 'sample' a buffet of avr-like genes from diverse sources in their coevolution with changing plant populations. Many avr genes have been known to be potentially mobile, because of their presence on plasmids (Vivian et al., "Avirulence Genes in Plant-Pathogenic Bacteria: Signals or Weapons?," *Microbiology* 143:693–704 (1997); Leach et al., "Bacterial Avirulence Genes," *Annul. Rev. Phytopathol,* 34:153–179 (1996), which are hereby incorporated by reference). Recent observations with *Pseudomonas syringae* highlight the apparent mobility of avr genes. Several *Pseudomonas syringae* avr genes are liked with transposable elements or phage sequences (Hanekamp et al., "Avirulence Gene D of *Pseudomonas syringae* pv. *Tomato* May Have Undergone Horizontal Gene Transfer," *FEBS Lett.,* 415:40–44 (1997), which is hereby incorporated by reference), and the hrp clusters in different strains of *Pseudomonas syringae*, although conserved in themselves, are bordered by a hypervariable region enriched in avr genes and mobile DNA elements.

Alternatively, the protein or polypeptide can be a protein or polypeptide which is not normally secreted by a type III secretion system, in which case the protein or polypeptide is expressed and secreted from the host cell as a fusion protein. The secretion signal, whether a mRNA or a polypeptide fragment, is linked to the protein or polypeptide of interest by an in-frame gene fusion, which preferably results in linking the mRNA or polypeptide fragment to the N-terminal end of the protein of polypeptide of interest. Such fusion proteins include a secretion signal linked to a protein or polypeptide of interest, for example, by a peptide bond between the secretion signal and the protein or polypeptide of interest. Fusion proteins can be prepared by ligating two or more DNA molecules together, one of which encodes the protein or polypeptide of interest and the other of which encodes the secretion signal. The two DNA molecules must be ligated in a manner which allows their proper expression. A number of efficient expression schemes for preparing fusion proteins have been developed and are well known in the art. According to one approach the fusion protein is prepared with a rotease cleavage site intermediate the protein or polypeptide of interest and the secretion signal, such that the secretion signal can be removed from the protein or polypeptide of interest by, for example, proteolytic cleavage following isolation of the fusion protein. A linker or spacer peptide may also be included to promote proteolytic cleavage (Polyak et al., "Introduction of Spacer Peptides N-terminal to a Cleavage Recognition Motif in Recombinant Fusion Proteins Can Improve Site-specific Cleavage," *Protein Eng.* 10(6):615–619 (1997), which is hereby incorporated by reference). A number of suitable proteases (e.g., factor Xa, chymosin, trypsin, etc.) and their protease-specific cleavage sites are known in the art, and others continually being identified. Any protease capable of cleaving a specific amino acid sequence without disrupting the protein or polypeptide of interest can be employed.

Thus, DNA molecules encoding a protein or polypeptide capable of being secreted by the type III secretion system can either be isolated (i.e., those encoding proteins that naturally contain a compatible secretion signal) or fabricated (i.e., those encoding for fusion proteins that contain a secretion signal linked by an in-frame gene fusion to a protein or polypeptide of interest). As indicated above, a single DNA construct of the present invention can contain both a type III secretion system and a sequence encoding a protein or polypeptide capable of secretion by the type III secretion system or a pair of DNA constructs can be employed.

Regardless of which approach is utilized, once the DNA molecule is constructed and obtained, it can be incorporated in cells using conventional recombinant DNA technology. Generally, this involves inserting the DNA molecule into an expression system to which the DNA molecule is heterologous (i.e., not normally present). Expression systems of the present invention contain an expression vector into which is inserted one or more heterologous DNA constructs of the present invention. The heterologous DNA molecule is inserted into the expression system or vector in proper sense orientation. The vector contains the necessary elements for the transcription of the DNA constructs of the present invention.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant or engineered genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology,* vol. 185 (1990), which is hereby incorporated by reference), and any derivatives thereof. Suitable vectors are continually being developed and identified. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual,* Cold Springs Laboratory, Cold Springs Harbor, N.Y. (1982), which is hereby incorporated by reference.

A variety of host-vector systems may be utilized to express the type III secretion system and the protein or polypeptide capable of secretion by the type III secretion system. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. Efficient translation of mRNA in prokaryotes requires a ribosome binding site called the Shine-Dalgamo ("SD") sequence on the mRNA. This sequence is a short nucleotide sequence of mRNA that is located before the start codon, usually ATG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. Thus, any SD-ATG combination that can be utilized by host cell ribosomes may be employed. Such combinations include, but are not limited to, SD-ATG combinations synthesized by recombinant techniques, the SD-ATG combination from the cro gene or the N gene of coliphage lambda, or from the *Escherichia coli* tryptophan E, D, C, B or A genes. For a review on maximizing gene expression; see Roberts and Lauer, *Methods in Enzymology,* 68:473 (1979), which is hereby incorporated by reference.

Promoters vary in their "strength" (i.e. their ability to promote transcription). For the purposes of expressing a cloned DNA construct of the present invention, it is desirable to use strong promoters in order to obtain a high level of transcription and, hence, expression of the DNA construct. Depending upon the host cell system utilized, any one of a number of suitable promoters may be used. For instance, when cloning in *Escherichia coli,* its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *Escherichia coli* promoters produced by recombinant DNA or other synthetic DNA techniques may be used to provide for transcription of the inserted construct.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Host cells can be transformed using the expression systems of the present invention, whereby the host cell is transformed with one or more of the DNA constructs of the present invention, as described above. Preferably, the host cells are present in a cell culture. Although any bacterial cell is suitable for use as a host cell, *Escherichia coli, Erwinia amylovora,* and *Erwinia chrysanthemi* are preferred host cells.

Biological markers can be used to identify the cells carrying recombinant DNA molecules. In bacteria, these are commonly drug-resistance genes. Drug resistance is used to select bacteria that have taken up cloned DNA from the much larger population of bacteria that have not. In the early mammalian gene transfer experiments involving viral genes, the transfer of exogenous DNA into cells was detected because the DNA had a biological activity, it led to production of infectious virus or produced stable changes in the growth properties of the transfected cells. It was then discovered that the DNA tumor virus, herpes simplex virus (HSV), contained a gene encoding the enzyme thymidine kinase (the tk gene). The HSV tk gene can be used as a selectable genetic marker in mammalian cells in much the same way that drug-resistance genes worked in bacteria, to allow rare transfected cells to grow up out of a much larger population that did not take up any DNA. The cells are transferred to selective growth medium, which permits growth only of cells that took up a functional tk gene (and the transferred DNA of interest). Various dominant selectable markers are now known in the art, including: aminoglycoside phosphotransferase (APH), using the drug G418 for selection which inhibits protein synthesis; the APH inactivates G418; dihydrofolate reductase (DHFR):Mtx-resistant variant, using the drug methotrexate (Mtx) for selection which inhibits DHFR; the variant DHFR is resistant to Mtx; hygromycin-B-phosphotransferase (HPH), using the drug hygromycin-B which inhibits protein synthesis; the HPH inactivates hygromycin B; thymidine kinase (TK), using the drug aminopterin which inhibits de novo purine and thymidylate synthesis; the TK synthesizes thymidylate; xanthine-guanine phosphoribosyltransferase (XGPRT), using the drug mycophenolic acid which inhibits de novo GMP synthesis; XGPRT synthesizes GMP from xanthine; and adenosine deaminase (ADA), using the drug 9-b-D-xylofuranosyl adenine (Xyl-A) which damages DNA; the ADA inactivates Xyl-A. Other selectable markers are continually being identified.

Other aspects of the present invention relate to methods of secreting a protein or polypeptide into the environment of a host cell. According to one embodiment, this method is performed by introducing into a host cell a DNA construct of the present invention which contains both a nucleic acid sequence encoding a functional type III secretion system and a nucleic acid sequence encoding a protein or polypeptide capable of being secreted by the type III secretion system. The DNA construct is introduced into the host cell under conditions effective to cause expression of the encoded protein or polypeptide, wherein the encoded protein or polypeptide is secreted by the host cell into the environment (i.e., culture medium). According to a second embodiment, this method is performed by introducing into a host cell a two DNA construct system of the present invention, one of which contains a nucleic acid sequence encoding a functional type III secretion system and the other of which contains a nucleic acid sequence encoding a protein or polypeptide capable of being secreted by the type III secretion system. The DNA constructs are introduced into the host cell under conditions effective to cause expression of the encoded protein or polypeptide and the type III secretion system, wherein the encoded protein or polypeptide is secreted by the host cell into the environment.

Another aspect of the present invention relates to a method of isolating a protein or polypeptide of interest. This method is performed by first providing a recombinant host cell that contains (i) a DNA molecule encoding a functional type III secretion system and (ii) a heterologous DNA molecule having a promoter operably coupled to a nucleic acid sequence encoding a protein or polypeptide capable of being secreted by the type III secretion system. The recombinant host cell is then introduced into a culture medium, where the encoded protein or polypeptide and the type III secretion system are expressed and the encoded protein or polypeptide is secreted into the culture medium, and the encoded protein or polypeptide is isolated from the culture medium.

The recombinant host cell can contain a homologous type III secretion system, in which case the encoded protein or polypeptide to be secreted is heterologous to both the host cell and the type III secretion system. As indicated above, the encoded protein or polypeptide can be a naturally secreted protein or a fusion protein. For example, an *Erwinia amylovora* host cell (which contains a homologous hrp secretion system) can be transformed with a heterologous DNA molecule that contains a promoter operably coupled to a sequence encoding an Avr protein of *Pseudomonas syringae*. When the recombinant *Erwinia amylovora* is grown on appropriate culture medium, the Avr protein is expressed and secreted into culture medium, from which it is then isolated.

Alternatively, the recombinant host cell can contain a heterologous type III secretion system and a heterologous protein or polypeptide coding DNA molecule. The DNA constructs of the present invention can be used to transform a host cell. For example, an *Escherichia coli* host cell can be transformed with a single construct of the present invention which contains a DNA sequence encoding a functional type III secretion system of *Erwinia chrysanthemi* and a DNA sequence encoding an Avr protein of *Pseudomonas syringae*. When the recombinant *Escherichia coli* host cell is grown on appropriate culture media, the Avr protein is expressed and secreted into culture medium, from which it is then isolated.

Effective conditions include optimal growth temperatures and nutrient media which will enable maximal growth of the host cells and maximal expression of the protein or polypeptide of interest. Examplary culture media include, without limitation, LM media and minimal media, both of which are known in the art. One of ordinary skill in the art can readily determine the optimal growth temperatures for particular strains of host cells and suitable nutrient media capable of optimizing host cell growth.

Purified protein may be obtained by several methods. The protein or polypeptide is preferably produced in purified form (preferably at least about 80%, more preferably 90%, pure) by conventional techniques. Since the recombinant host cells express a type III secretion system, the protein or polypeptide is secreted into the growth medium of recombinant host cells. In such cases, to isolate the protein, the recombinant host cells are propagated, the growth medium is centrifuged to separate cellular components from supernatant containing the secreted protein or polypeptide, and the supernatant is removed. The supernatant is then subjected to sequential ammonium sulfate precipitation. The fraction containing the polypeptide or protein is subjected to gel filtration in an appropriately sized dextran or polyacrylamide column to separate the proteins. If necessary, the protein fraction may be further purified by HPLC.

Where the protein or polypeptide of interest is a fusion protein containing a protease-cleavable amino acid sequence between a secretion signal and a protein or polypeptide of interest, it is possible to isolate the fusion protein, expose the isolated fusion protein to a protease, and then recover (i.e., purify) the protein or polypeptide of interest as described above. Alternatively, to avoid repetitive purification steps, it is possible to introduce a protease into the culture medium or supernatant (i.e., following separation of the cellular component from the culture medium) prior to purification. After treatment with the protease, the protein or polypeptide of interest can be purified as described above.

Because the constructs and systems of the present invention enable expression of a protein or polypeptide and its secretion into an environment (e.g., culture medium) of the host cell which contains the construct or system, the present invention offers significant advantages in isolating a protein or polypeptide of interest. These advantages include the ability to dispense with disruption of the host cell membrane (i.e., by sonication or other known methods) to cause release of cellular contents into the culture medium and, thus, the ability to dispense with costly purification schemes for removal of cellular debris. By avoiding these practices, significant cost savings and significant improvements in protein or polypeptide purity can be recognized.

Another aspect of the present invention relates to the ability to utilize the type III secretion system in a novel manner to prospect for putative effector proteins or polypeptides. As indicated previously, Avr proteins are one type of effector protein which have significant potential for use, for example, in the field of agriculture. However, prior art methods of identifying potential effector proteins have proven to be inefficient.

Accordingly, this aspect of the present invention relates to a method of identifying a gene encoding a potential effector protein or polypeptide. This method is performed by first providing a host cell that contains a DNA molecule encoding a functional type III secretion system. A gene to be screened (i.e., a candidate), which encodes a protein or polypeptide, is introduced into the host cell under conditions effective to express the encoded protein or polypeptide. Next, secretion of the encoded protein or polypeptide by the recombinant host cell is determined. Secretion of the encoded protein or polypeptide (i.e., via the type III secretion system) indicates that the gene encodes a potential effector protein or polypeptide.

The recombinant host cell can contain a homologous type III secretion system, in which case the gene to be screened is heterologous to both the host cell and the type III secretion system. For example, an *Erwinia amylovora* host cell (which contains a homologous hrp secretion system) can be transformed with a heterologous gene obtained from *Pseudomonas syringae*.

Alternatively, the recombinant host cell can contain a heterologous type III secretion system and a heterologous gene to be screened. For example, an *Escherichia coli* host cell can be transformed with a DNA construct that contains a DNA sequence encoding a functional type III secretion system of *Erwinia chrysanthemi* and a DNA sequence encoding a gene obtained from *Pseudomonas syringae*. (Also, co-transformation of the host cell with two separate constructs can be performed.)

A preferred approach for determining whether the protein or polypeptide is expressed and secreted utilizes a chimeric gene that encodes an epitope tag fused to the protein or polypeptide. The gene to be screened can be a specific protein-coding gene or it can be obtained via shotgun cloning techniques. Regardless of how the gene is obtained, it is then modified, for example, according to the procedures of Gopalan et al., *Plant Cell,* 8:1095–1105 (1996), which is hereby incorporated by reference, to prepare the chimeric gene. The chimeric gene is prepared in a manner which preferably results in location of the epitope tag at the C-terminal end of the fusion protein. The recombinant host cell is grown in a suitable culture medium and then all protein secreted by the recombinant host cell is isolated and, preferably, immobilized. The isolated protein is then exposed to an immunodetection assay capable of recognizing the epitope tag.

Preferably the immunodetection assay utilizes a double antibody recognition complex, with the first antibody recognizing the epitope tag and the second antibody, which bears a detectable label, recognizing the first antibody. Together, the two antibodies enable detection of the epitope-tagged protein or polypeptide.

Monoclonal antibody production may be effected by techniques which are well-known in the art. A description of the theoretical basis and practical methodology for preparing hybridomas is set forth in Kohler and Milstein, Nature 256:495 (1975), which is hereby incorporated by reference. Procedures for raising polyclonal antibodies are also well known, including procedures disclosed in E. Harlow, et. al., editors, Antibodies: A Laboratory Manual (1988), which is hereby incorporated by reference. In addition to utilizing whole antibodies, the processes of the present invention encompass use of binding portions of such antibodies. Such binding portions include Fab fragments, F(ab')2 fragments, and Fv fragments. These antibody fragments can be made by conventional procedures, such as proteolytic fragmentation procedures, as described in Goding, Monoclonal Antibodies: Principles and Practice, pp. 98–118, New York:Academic Press (1983), which is hereby incorporated by reference.

Examples of labels useful for diagnostic imaging in accordance with the present invention are radioactive labels, fluorescent labels, nuclear magnetic resonance active labels, positron emitting isotopes detectable by a positron emission tomography ("PET") scanner, chemiluminescent labels, and enzymatic markers. A number of labels are well known in the art and others are continually being identified.

This method of screening for putative effector proteins enables one of ordinary skill in the art to more readily identify putative effector proteins, which can then be tested on host organisms to determine the ability of the putative effector protein to induce a host plant response.

These aspects of the present invention are further illustrated by the examples below.

EXAMPLES

The following examples are provided to illustrate embodiments of the present invention but they are by no means intended to limit its scope.

Materials and Methods

Bacterial Strains, Culture Conditions, and DNA Manipulation Techniques

Bacterial strains and plasmids used in this study are listed in Table 1 below.

TABLE 1

Bacterial Strains and Plasmids

| Designation | Relevant Characteristics and Use | Reference or Source |
| --- | --- | --- |
| *Escherichia coli* | | |
| DH5α | SupE44 ΔlacU169 (f80 lacZΔM15) hsdR17 recA1 endA1 gyrA96 thi-1 relA1, NX$^r$ | Life Technologies |
| XLOLR | Δ(mcrA)183 Δ(mcrBc-hsdSMR-mrr)173 endA1 thi-1 recA1 gyrA96 relA1 lac [F' proAB laqI$^q$ZΔM15 Tn10(Tc$^r$)] | Stratagene |
| SM10 λpir | SM10 lysogenized with λ-pir for mobilizing pUT:: mini-Tn5Cm, Km$^r$ | (Miller et al., J. Bacteriol., 170: 2575–2583 (1988), which is hereby incorporated by reference) |
| MC4100 | F' araD139 Δ(argF-lacZYA) U169 rpsL 150 relA1 flb-5301 ptsF25 deoC1 | (Casadaban, J. Mol. Biol. 104:541–555 (1976), which is hereby incorporated by reference) |
| Plasmids | | |
| pFLAG-CTC | For construction of C-terminal fusion to FLAG peptide, Ap$^r$ | Kodak Scientific Imaging Systems |
| pUT::mini- | Mini-Tn5 transposon with Cm$^r$ on | (de Lorenzo et al., J. Bacteriol., |

TABLE 1-continued

Bacterial Strains and Plasmids

| Designation | Relevant Characteristics and Use | Reference or Source |
|---|---|---|
| Tn5Cm | suicide plasmid pGP704 derivative for transposon mutagenesis, Ap$^r$ | 172:6568–6572 (1990), which is hereby incorporated by reference) |
| pML123 | Broad host range expression vector for cloning avrPto-FLAG, Gm$^r$ | (Labes et al., Gene, 89:37–46 (1990), which is hereby incorporated by reference) |
| pPtE6 | An avrPto clone in pDSK519, Km$^r$ | (Ronald et al., J. Bacteriol. 174: 1604–1611 (1992), which is hereby incorporated by reference) |
| pHIR11 | pLAFR3 carrying Pss61 hrp/hrc cluster, Tc$^r$ | (Huang et al., J. Bacteriol., 170: 4748–4756 (1988), which is hereby incorporated by reference) |
| pCPP2156 | pCPP19 carrying E. chrysanthemi hrp cluster, Sp$^r$ | This work |
| pCPP2157 | pCPP19 carrying E. chyrsanthemi hrp cluster, Sp$^r$ | (Bauer et al., MPMI 8:484–491 (1995), which is hereby incorporated by reference) |
| pCPP2329 | pFLAG-CTC carrying avrPto, Ap$^r$ | This work |
| pAVRB-FLAG2 | pML 123 carrying avrB-FLAG, Gm$^r$ | (Gopalan et al., Plant Cell, 8:1095–1105 (1996), which is hereby incorporated by reference) |
| pAVRB1 | pDSKS19 carrying avrB, Km$^r$ | (Tamaki et al., J. Bacteriol. 170:4846–4854 (1988), which is hereby incorporated by reference) N.T. Keen |
| pAVRPTO-FLAG | pML 123 carrying avrPto-FLAG, Gm$^r$ | This work |
| pCPP2368 | A pCPP2156:: Tn5Cm that has HR$^-$ phenotype, Sp$^r$, CM$^r$ | This work |
| pCPP2416 | A pCPP2156:: Tn5Cm that has HR$^+$ phenotype, Sp$^r$, Cm$^r$ | This work |
| pCPP2318 | pCPP30 carrying mature blaM, Tc$^r$ | (Charkowski et al., J. Bacteriol. 179:3866–3874 (1997), which is hereby incorporated by reference) |

*Escherichia coli* strains were routinely grown in LM medium (Hanahan, D., *J. Mol. Biol.*, 166:557–580 (1983), which is hereby incorporated by reference) at 37° C. for isolation of plasmids and at 30° C. for protein secretion assays. The following concentrations of antibiotics were used in selective media: ampicillin (Ap), 100 Ag/ml; chloramphenicol (Cm), 20 μg/ml; gentamycin (Gm), 10 μg/ml; kanamycin (Km), 50 μg/ml; nalidixic acid (Nx), 20 μg/ml; spectinomycin (Sp), 50 μg/ml; tetracycline (Tc), 10 μg/ml. Standard procedures were followed by DNA manipulations (Sambrook, J., et al., Molecular Cloning: A Laboratory Manual, 2$^{nd}$ Edition (Cold Spring Harbor Laboratory Press, Cold Spring Harbor, N.Y.), pp Pages (1989), which is hereby incorporated by reference).

Mini-Tn5Cm Mutagenesis of the hrp Gene Cluster in pCPP2156

Mini-Tn5Cm mutagenesis of *Escherichia coli* DH5α (pCPP2156) was initiated by conjugation with *Escherichia coli* SM10λpir (pUT::mini-Tn5Cm). Because pUT cannot replicate in *Escherichia coli* DH5α, Cm$^r$ transconjugants have mini-Tn5Cm transposed to the chromosome or pCPP2156. To obtain a pool of pCPP2156::mini-Tn5Cm plasmids, all Cm$^r$ colonies were triparentally mated with *Escherichia coli* XLOLR (Tc$^r$). The cosmids from *Escherichia coli* XLOLR transconjugants, selected on LM agar containing Tc, Sp, and Cm, were isolated and their restriction fragment patterns compared with each other and pCPP2156. All 46 cosmids initially examined contained random insertions of mini-Tn5Cm in pCPP2156. Two primers were used to sequence from both ends of mini-Tn5Cm including a first primer having a nucleotide sequence corresponding to SEQ. ID. No. 3 as follows:

AGATCTGATC AAGAGACAG                19 and a second primer having a nucleotide sequence corresponding to SEQ. ID. No. 4 as follows:

CCGTGTGTAT AAGAGTCAG                19

Based on restriction mapping and DNA sequencing from both ends of mini-Tn5Cm, two different pCPP2156:mini-Tn5Cm derivatives were chosen. In one of them, Tn5Cm was inserted in the intergenic region between hrpJ and hrcV in the hrpJ operon. This cosmid was named pCPP2368. The other cosmid contained mini-Tn5Cm outside of the hrp cluster and was named pCPP2416. Both cosmids were electroporated into *Escherichia coli* DH5α.

Plant Bioassays

Tobacco (*Nicotiana tabacum* L. cv. Xanthi) and *Nicotiania clevelandii* were grown under greenhouse conditions and then maintained in the lab at room temperature with daylight and supplemental metal halide illumination for HR assays. Soybean (*Glycine max* L.) and tomato (*Lycopersicum esculentum* Mill. cv. Rio Grande) plants were grown from seeds in pots with Cornell Mix (Cornell University) in the lab at room temperature. *Escherichia coli* DH5α cells grown overnight on LM plates were washed twice with 5mM MES (morpholinoethanesulfonic acid, pH 6.5) by centrifugation and then resuspended in an appropriate volume of the same buffer to an OD$_{600}$ of 0.8 (experiments involving avrPto used *Escherichia coli* MC4100 and a 3-fold higher level of inoculum). Previously described procedures were used for the infiltration of bacterial cells into tobacco, tomato and *Nicotiana clevelandii* leaves (Bauer et al., *MPMI*, 7:573–581 (1994), which is hereby incorporated by reference) and soybean leaves (Gopalan et al., *Plant Cell*, 8:1095–1105 (1996), which is hereby incorporated by reference).

Preparation of AvrB Antibodies

AvrB-FLAG was purified from *Escherichia coli* DH5α (pFLAG-CTC::AvrB) by affinity chromatography as described (Gopalan et al., *Plant Cell*, 8:1095–1105 (1996), which is hereby incorporated by reference), followed by precipitation of aliquots containing 1 mg of partially purified protein with trichloroacetic acid ("TCA") (20% final concentration), resuspension in SDS polyacrylamide gel loading buffer (Sambrook, J., et al., Molecular Cloning: A Laboratory Manual, 2$^{nd}$ Edition (Cold Spring Harbor Laboratory Press, Cold Spring Harbor, N.Y.), (1989), which is hereby incorporated by reference), and electrophoresis on 1.5 mm×11 cm×10 cm 12% polyacrylamide preparative gels. The AvrB band was excised from each gel following brief staining with a solution of 0.2% Coomassie R350 (Pharmacia Biotech) dissolved in water. Subsequent extraction of AvrB from the gel matrix and generation of polyclonal rabbit anti-AvrB antisera were performed by the Immunological Resource Center at the University of Illinois, Urbana Ill. Prior to usage, the antisera was delipified with sodium dextran sulfate (average molecular weight of 500,000) to a final concentration of 0.25% and CaCl$_2$ to a final concentration of 1.0% followed by incubation of 4° C. for 8–12 hours (Walton, K.W., et al., *J. Clin. Pathol.*, 17:627–643 (1964), which is hereby incorporated by reference). This mixture was clarified by centrifugation at 12,000×g at 4° C. for 10 minutes. Proteins were precipitated by the addition of ammonium sulfate at 50% saturation, followed by incubation at 4° C. for 8–12 hours, and then collected by centrifugation at 12,000×g at 4° C. for 10 minutes and resuspended in their original volume with phosphate-buffered saline.

Construction of pAVRPTO-FLAG

The avrPto gene was isolated by polymerase chain reaction ("PCR") with Pfu DNA polymerase (Stratagene, La Jolla, Calif.) and pPtE6 as the template. The upper primer had a nucleotide sequence that contains an Nde I site, corresponding to SEQ. ID. No. 5 as follows:

GAGCGAGCAT ATGGGAAATA TATGTGTCGG C    31

The lower primer had a nucleotide sequence that contains an Sal I site, corresponding to SEQ. ID. No. 6 as follows:

ATTGTAGTCG ACTTGCCAGT TACGGTACGG G    31

The reaction products from 30 PCR cycles were resolved by electrophoresis through 0.7% agarose, and the avrPto DNA was isolated using an Eluquick kit (Schleicher & Schuell), followed by digestion with Nde I and Sal I. This DNA was cloned into pFLAG-CTC, previously digested with Nde I and Sal I, and named pCPP2329. The avrPto-FLAG DNA was isolated from pCPP2329 by digestion with Ssp I and cloned into pML 123, which had been previously digested with BamH I and blunted with Klenow polymerase, producing pAVRPTO-FLAG. As with avrB-FlaG2 (Gopalan, S., et al., *Plant Cell,* 8:1095–1105 (1996), which is hereby incorporated by reference), avrPto-FLAG is expressed by both the tax promoter (from pFLAG-CTC) and the pML 123 nptII promoter, thus permitting constitutive expression in LM medium and in planta.

Preparation of Protein Samples From Supernatant and Cell Fractions

Bacteria grown overnight on LM plates at 37° C. were washed twice by centrifugation and resuspended in LM broth. Each bacterial suspension was diluted to $OD_{600}$=0.2 in 40 ml of LM broth containing appropriate antibiotics and cultured at 30° C. in a rotary shaking incubator at 220 rpm until the $OD_{600}$ reached 0.8. Centrifugations for the separation of bacterial cultures into cell-bound and supernatant fractions were performed with an SS-34 rotor (DuPont Instrument) at 4° C.

Forty milliliters of culture was initially centrifuged at 6,000 rpm (>4300×g) for 15 minutes. For the supernatant fraction, the upper 20 ml of supernatant was carefully transferred to a new centrifuge tube and further centrifuged at 12,000 rpm (>17200×g) for 40 minutes, followed by transfer of the upper 10 ml of supernatant to a new tube. Six milliliters of 25% TCA was added to the supernatant fraction, which was then kept on ice for 3–4 hours, followed by centrifugation at 12,000 (>17200×g) rpm for 40 minutes. The pellet was subsequently washed with 20 ml of ice-cold acetone and then resuspended in 200 μl or 100 μl×SDS sample buffer (New England Biolabs). For the cell fraction, the pellet from the initial centrifugation was resuspended in 4 ml of LM broth. One hundred microliters of bacterial cell suspension was mixed with 50 μl of 3×SDS sample buffer. Each protein sample was held in a boiling water bath for 5 minutes before electrophoresis, and then 15 μl of each sample was loaded onto the gel.

Immunoblot Analysis

Protein samples were separated by electrophoresis through a 10% SDS-polyacrylamide gel. Proteins in the gel were then electrotransferred to Immobilon-P membrane (Millipore Corp.) with a Semi-Phor system (Hoefer Scientific Instruments). AvrB-FLAG and AvrPto-FLAG were detected with the Western-Light Plus kit (Tropix) using anti-FLAG M2 antibodies (Kodak Scientific Imaging Systems) and anti-mouse IgG alkaline phosphatase conjugate (Sigma) as primary and secondary antibodies, respectively. AvrB and β-lactamase were detected with the same system except using anti-AvrB antibodies or anti-β-lactamase antibodies (5 prime→3 prime) and anti-rabbit IgG alkaline phosphatase conjugate (Sigma) as primary and secondary antibodies, respectively.

Primers, DNA Sequencing and Data Analysis

Oligonucleotide synthesis and DNA sequencing were performed at the Cornell Biotechnology Center. DNA sequence data were managed and analyzed with the DNAStar Program (DNAStar, Madison, Wis.).

Example 1

Preparation of Cosmid pCPP2156, Which Carries an Intact *Erwinia chrysanthemi* hrp Gene Cluster Several cosmids carrying *Erwinia chrysanthemi* EC16 hrp genes were previously isolated on the basis of their ability to hybridize with an *Erwinia amylovora* DNA fragment carrying the hrpJ operon (Bauer, D. W., et al., *MPMI,* 7:573–581 (1994), which is hereby incorporated by reference). One of these cosmids, pCPP2157, is shown in FIG. 1 and was subsequently found to carry also hrpN and the complete hrpC operon (Bauer, et al., "*Erwinia chrysanthemi* harpin$_{Ech}$: An Elicitor of the Hypersensitive Response that Contributes to Soft-rot Pathogenesis," 8:484–491 (1995); Kim, et al., "The hrpC and HrpN Operons of *Erwinia chrysanthemi* EC16 are Flanked by plcA and Homologs of Hemolysin/Adhesion Genes and Accompanying Activator/Transporter Genes," *MPMI,* 11 (6):563–567 (1998), which are hereby incorporated by reference). Although pCPP2157 appeared to carry both borders of the *Erwinia chrysanthemi* hrp cluster, *Escherichia coli* (pCPP2157) failed to elicit an HR in tobacco leaves. DNA sequencing of the right end of the pCPP2157 insert revealed that hrcU was missing the last 180 nucleotides, as suggested by comparison with the *Erwinia amylovora* hrcU gene (Bogdanove, et al., "*Erwinia amylovora* Secretes Harpin via a Type III Pathway and Contains a Homolog of YopN of Yersinia spp.," *J. Bacteriol.,* 178:1720–1730 (1996), which is hereby incorporated by reference). hrcU is one of nine former hrp genes that encode core components of the type III secretion system, are broadly conserved in plant and animal pathogenic bacteria, and have been renamed as hrc (HR and conserved) genes (Bogdanove, et al., *Mol. Microbiol.,* 20:681–683 (1996), which is hereby incorporated by reference). Because of the hrcU truncation, additional cosmids hybridizing with probes carrying hrpn and hrcU were analyzed. pCPP2156 was one of those. Partial DNA sequence analysis and physical map comparisons with the *Erwinia amylovora* hrp genes suggested that pCPP2156 carried the entire *Erwinia chrysanthemi* hrp gene cluster, including at least one intercalated region not obviously related to Hrp function and 14-kb of additional DNA beyond hrcU (FIG. 1). However, pCPP2156 failed to elicit an HR in tobacco.

Example 2

*Escherichia coli*(pCPP2156) Enables Elicitation of an AvrB-dependent HR in *Nicotiana clevelandii* and Soybean Cultivar Norchief The plasmid pHIR11, which carries the intact *Pseudomonas syringae* pv *syringae* 61 hrp cluster, enables *Escherichia* coli to elicit an HR in tobacco, because it also carries hrmA, an avr-like gene whose transient expression in tobacco cells is lethal (Alfano, et al., *Mol. Microbiol.*, 19:715–728 (1996); Alfano, et al., *MPMI*, 10:580–588 (1997), which are hereby incorporated by reference). This suggested the possibility that pCPP2156 failed to elicit an HR in tobacco because it did not carry an appropriate avr gene. To test this, pAVRB-FLAG2 was transformed into *Escherichia coli* DH5α cells carrying either pCPP2156 or pCPP2157. pAVRB-FLAG2 expresses the *Pseudomonas syringae* pv *glycinea* avrB gene such that the product has an eight-amino acid FLAG epitope C-terminal fusion (Gopalan, et al., *Plant Cell*, 8:1095–1105 (1996), which is hereby incorporated by reference). Transformants were infiltrated at a concentration of $5 \times 10^8$ cfu/ml into *Nicotiana clevelandii*, a plant that reacts hypersensitively to Hrp+ bacteria carrying avrB. A typical HR developed within 24 hours in panels inoculated with bacteria carrying both avrB and pCPP2156, but there was no response in panels inoculated with bacteria lacking avrB or carrying an incomplete hrp cluster (FIG. 2), or inoculated with bacteria carrying only pAVRB-FLAG2.

The failure of *Escherichia coli*(pCPP2157, pAVRB-FLAG2) to elicit an HR in *Nicotiana clevelandii* suggested that this ability was Hrp-dependent. However, an explanation based on differences in the DNA flanking the hrp gene clusters in pCPP2156 and pCPP2157 remained a formal possibility. To resolve this, pCPP2156 was mutated with mini-Tn5Cm and two derivatives were isolated. Restriction mapping and DNA sequence analysis revealed that pCPP2416 and pCPP2368 carried insertions in the 14-kb region beyond hrcU and in the intergenic region between hrpJ and hrcV, respectively (FIG. 1). The mutation in pCPP2368 would be expected to block transcription of hrcV and downstream genes in the putative hrpJ operon, and a polar mutation in the hrpJ operon of *Pseudomonas syringae* pv *syringae* 61 has been shown to result in accumulation of the HrpZ harpin within the bacterial cytoplasm (Charkowski et al., "Altered Localization of HrpZ in *Pseudomonas syringae* pv. *syringae* hrp Mutants Suggests That Different Components of the Type III Secretion Pathway Control Protein Translocation Across the Inner and Outer Membranes of Gram-negative Bacteria," *J. Bacteriol.*, 179:3866–3874 (1997), which is hereby incorporated by reference). *Escherichia coli* cells carrying pCPP2416 and pCPP2368 were transformed with pAVRB-FLAG2 and tested for their ability to elicit the HR in *Nicotiana clevelandii*. An HR was observed only with *Escherichia coli* (pCPP2416, pAVRB-FLAG2) (FIG. 2).

To further test the ability of *Escherichia coli* (pCPP2156) to elicit an avrB-dependent HR, the leaves of soybean cultivars Norchief (RPGI) and Acme (rpgl) were infiltrated with bacteria carrying various plasmids. RPGI is an R gene that interacts in a gene-for-gene manner with avrB (Staskawicz, et al., *J. Bacteriol.*, 169:5789–5794 (1987), which is hereby incorporated by reference). The HR was observed only in Norchief inoculated with bacteria carrying both avrB and an intact hrp cluster.

Example 3

*Escherichia coli*(pCPP2156) Secretes AvrB in Culture in a Hrp-dependent Manner While Retaining β-lactamase The secretion of Avr proteins by *Pseudomonas syringae* is presumed to be dependent on host cell contact, because Avr proteins remain cytoplasmic in culture even when the Hrp system is actively secreting harpins (Alfano, et al., *J. Bacteriol.*, 179:5655–5662 (1997), which is hereby incorporated by reference). The seemingly less specialized interaction of *Erwinia chrysanthemi* with its hosts suggested the possibility that Avr secretion may be regulated less tightly. To test this, FLAG epitope-tagged AvrB encoded by pAVRB-FLAG2 was used to determine if *Escherichia coli* (pCPP2156) could secrete AvrB in culture. Bacterial cultures in late logarithmic-phase growth were separated into supernatant and cell-bound fractions by centrifugation, and then proteins in both fractions were resolved by SDS-PAGE. AvrB-FLAG was visualized by immunoblotting with anti-FLAG monoclonal antibodies and chemiluminescent detection. AvrB-FLAG was found in the supernatant of *Escherichia coli*(pCPP2156) (FIG. 3). Although much of the AvrB remained in the cell-bound fraction, secretion was Hrp-dependent and specific in that no AvrB-FLAG was found in the supernatant of *Escherichia coli* (pCPP2368) (FIG. 3), and Coomassie staining revealed equally low levels of protein in the supernatant fractions of all of the bacteria tested.

To confirm that the presence of AvrB-FLAG in the *Escherichia coli*(pCPP2156) medium resulted from specific secretion and not cell lysis, and that secretion was not due to FLAG epitope, the localization of AvrB and mature β-lactamase was simultaneously monitored (FIG. 4). *Escherichia coli* cells carrying pCPP2156 or pCPP2368 were first transformed with pAVRb1, which expresses AvrB from the lac promoter (Tamaki, S., et al., *J. Bacteriol.*, 170:4846–4854 (1988), which is hereby incorporated by reference), and pCPP2318, which encodes a mature β-lactamase that lacks its N-terminal signal peptide and can be used as a cytoplasmic marker (Charkowski et al., "Altered Localization of HrpZ in *Pseudomonas syringae* pv. *syringae* hrp Mutants Suggests That Different Components of the Type III Secretion Pathway Control Protein Translocation Across the Inner and Outer Membranes of Gram-negative Bacteria," *J. Bacteriol.*, 179:3866–3874 (1997), which is hereby incorporated by reference). The distribution of AvrB and β-lactamase in the same supernatant and cell-bound fraction samples was monitored by immunoblotting with appropriate antibodies. The *Escherichia coli* (pCPP2156) supernatant sample contained AvrB but no β-lactamase (FIG. 4), indicating that AvrB secretion occurred without the FLAG epitope and without cell lysis.

Example 4

*Escherichia coli*(pCPP2156) Secretes AvrPto in Culture in a Hrp-dependent Manner The evidence for Avr action inside plant cells following Hrp-dependent transfer is strongest with AvrPto, whose structural gene was originally isolated from *Pseudomonas syringae* pv. *tomato* (Alfano, et al., *J. Bacteriol.*, 179:5655–5662 (1997); Tang, et al., *Science*, 274:2060–2062 (1996); Scofield, et al., *Science*, 274:2063–2065 (1996); Ronald, et al., *J. Bacteriol.*, 174:1604–1611 (1992), which are hereby incorporated by reference). Consequently, AvrPto was selected to test whether the ability of *Escherichia coli*(pCPP2156) to deliver *Pseudomonas syringae* Avr signals in planta and to secrete Avr proteins in culture would extend beyond AvrB. First, the construct pAVRPTO-FLAG, which encodes AvrPto with a C-terminal FLAG epitope fusion, was prepared. *Escherichia coli* cells carrying pAVRPTO-FLAG and pCPP2156 (but not pAVRPTO-FLAG alone, pCPP2156 alone, or pAVRPTO-FLAG with pCPP2368) elicited an HR in tomato cultivar Rio Grande carrying the Pto resistance gene. The secretion of AvrPto was determined with the same methods used for AvrB-FLAG and AvrB. AvrPto-FLAG was secreted by *Escherichia coli*(pCPP2156) but not by *Escherichia coli* (pCPP2157) or *Escherichia coli*(pCPP2368) (FIG. 5). Thus, secretion of AvrPto-FLAG was Hrp-dependent, and it also occurred without leakage of β-lactamase. In contrast, no AvrPto-FLAG was found in the supernatant of *Escherichia coli*(pHIR11), which expresses the intact *Pseudomonas syringae* Hrp system (FIG. 5).

The isolation of a cluster of *Erwinia chrysanthemi* hrp genes that directs *Escherichia coli* to secrete *Pseudomonas syringae* Avr proteins in culture and deliver Avr signals in planta has several implications for the pathogenic biology of *Erwinia chrysanthemi* and *Pseudomonas syringae*. As representative necrotrophic and biotrophic parasites, respectively, these two bacteria mark the extremes in the pathogenic personalities of the common gram-negative phytopathogenic bacteria. Nevertheless, it is possible that they elicit the HR and initiate parasitic attack in fundamentally similar ways, that they may be able to interchange their avr genes without loss of function, and that their cloned hrp clusters can be used to biochemically investigate Avr protein secretion and to systematically prospect for the proteins injected into plants by many plant pathogenic bacteria.

*Erwinia chrysanthemi* and *Pseudomonas syringae* appear to elicit the HR by the same mechanism in that their cloned hrp clusters are dependent on an appropriate avr gene for elicitation of the HR when heterologously expressed in nonpathogens. Thus, cosmid pHIR11 (*Pseudomonas syringae* hrp cluster) directs HR elicitation in tobacco, because it carries the avr-like hrmA gene. Cosmid pCPP2156 (*Erwinia chrysanthemi* hrp cluster) fails to elicit the Hr in tobacco, *Nicotiana clevelandii*, soybean, or tomato because it does not carry an avr gene that is recognized by these plants, but when provided with avrB or avrPto it appropriately directs elicitation of the HR in *Nicotiana clevelandii*, soybean cultivar Norchief, and tomato cultivar Rio Grande. This has two implications regarding HR elicitation by *Erwinia chrysanthemi*. First, the harpin encoded by pCPP2156, like that encoded by pHIR11, is apparently insufficient for bacterial HR elicitation (although both harpins can elicit programmed cell death when delivered exogenously) (Bauer, et al., "*Erwinia chrysanthemi* harpin$_{Ech}$: An Elicitor of the Hypersensitive Response that Contributes to Soft-rot Pathogenesis," 8:484–491 (1995); He, et al., *Cell,* 73:1255–1266 (1993), which are hereby incorporated by reference). Second, *Erwinia chrysanthemi* must carry avr genes somewhere outside the region cloned in pCPP2156 because it is able to elicit a Hrp-dependent HR in tobacco without provision of a heterologous avr gene (Bauer, et al., *MPMI,* 7:573–581 (1994), which is hereby incorporated by reference).

*Erwinia chrysanthemi* hrp mutants also are reduced in their ability to elicit infection at low levels of inoculum. Because it now appears that the primary function of the Hrp system is to deliver Avr-like proteins to host cells, identifying these proteins and determining their function will be key to understanding how *Erwinia chrysanthemi* initiates infection. Recent observations with *Erwinia amylovora* indicate that homologous avr-like genes are present in Erwinia spp. and *Pseudomonas syringae* (Gaudriault, et al., *Mol. Microbiol.,* 26:1057–1069 (1997); Bogdanove, et al., *Proc. Natl. Acad. Sci. USA,* 95:1325–1330 (1998), which are hereby incorporated by reference). Specifically, dspE, which is required for the pathogenicity of *Erwinia amylovora,* is a homolog of avrE, a gene that contributes quantitatively to the virulence of *Pseudomonas syringae* pv *tomato* strain PT23 on tomato and has an Avr phenotype in *Pseudomonas syringae* pv *glycinea* when tested on a variety of soybean cultivars (Lorang, et al., *MPMI,* 7:508–515 (1994); Lorang, et al., *MPMI,* 8:49–57 (1995), which are hereby incorporated by reference). The ability of avrE to restore the pathogenicity of an *Erwinia amylovora* dspE mutant provides direct evidence that a *Pseudomonas syringae* avr gene can function biologically in an Erwinia background. (Bogdanove, et al., *Proc. Natl. Acad. Sci. USA,* 95:1325–1330 (1998), which is hereby incorporated by reference). Furthermore, DspE-specific antibodies and appropriate hrp mutants have been used to establish that *Erwinia amylovora* secretes DspE in a Hrp-dependent manner in culture (Bogdanove, et al., *J. Bacteriol.* 180:2244–2247 (1998), which is hereby incorporated by reference). However, it is not known whether AvrE can be secreted in culture by *Erwinia amylovora* (or *Pseudomonas syringae*) or whether DspE and AvrE function inside plant cells.

The regulation of the *Erwinia chrysanthemi* Hrp system appears more relaxed in two ways in comparison with host-specific pathogens like *Pseudomonas syringae*. First, the *Erwinia chrysanthemi* hrp genes are not repressed by complex media (which enhances the utility of the system for secretion studies) (Collmer, et al., in "Advances in Molecular Genetics of Plant-Microbe Interactions," Vol. 3 ed. Daniels, M. J. (Kluwer, Dordrecht), pp. 49–56 (1994), which is hereby incorporated by reference). Second, the *Erwinia chrysanthemi* Hrp system does not appear to be gated in culture with respect to the secretion of Avr proteins. Although the *Pseudomonas syringae* hrp cluster carried on pHIR11 enables delivery of AvrB and AvrPto signals (presumably the Avr proteins themselves) to plant cells, it does not direct secretion of these proteins in culture (FIG. 5) (Gopalan, et al., *Plant Cell,* 8:1095–1105 (1996), which is hereby incorporated by reference). Because *Erwinia chrysanthemi* and *Pseudomonas syringae* possess similar Hrp systems (both in group I) (Alfano, et al., *J. Bacteriol.,* 179:5655–5662 (1997); Kim, et al., "The hrpC and hrpN Operons of *Erwinia chrysanthemi* EC16 are Flanked by plcA and Homologs of Hemolysin/Adhesion Genes and Accompanying Activator/Transporter Genes," *MPMI* 11(6): 563–567 (1998), which are hereby incorporated by reference), comparisons and genetic exchanges between them are likely to be useful for elucidating the mechanisms controlling Avr protein secretion in *Pseudomonas syringae*.

There is yet no direct evidence for the Hrp-mediated transfer of any Avr protein into plant cells, although the indirect evidence for this is particularly compelling with AvrB and AvrPto, as discussed above. The observation that these two proteins can travel the Hrp pathway to the bacterial milieu now provides direct confirmation of the first step in the translocation process. More importantly, the targeting signals controlling secretion and other aspects of the secretion process now can be explored in vitro. In this regard, the differing traffic specificities of the type II and type III protein secretion systems of *Erwinia chrysanthemi* are noteworthy, especially since both systems function heterologously in *Escherichia coli*. The cloned cluster of out (type II secretion) genes from *Erwinia chrysanthemi* EC16 directs the secretion of pectate lyase isozymes expressed from *Erwinia chrysanthemi* pel genes but not from *Erwinia carotovora* pel genes (He, et al., *Proc. Natl. Acad. Sci. USA,* 88:1079–1083 (1991), which is hereby incorporated by reference). This species-specific secretion occurs despite the fact that the Out systems and some of the Pels of these two species are homologous (Lindeberg, et al., *Mol. Microbiol.,*

20:175–190 (1996), which is hereby incorporated by reference). The construction of hybrid Pels has shown that the targeting information controlling species-specific secretion resides in the tertiary structure of these proteins (Lindeberg, et al., *J. Bacteriol.* 180:1431–1437 (1998), which is hereby incorporated by reference). In contrast, the *Erwinia chrysanthemi* Hrp (type III) system lacks even genus-specificity for its traffic, and the secreted proteins may be devoid of targeting information. This is based on the possibility that targeting information resides in the mRNA encoding the N-termini of these proteins, as has been demonstrated recently for the YopE and YopN proteins secreted by the Yersinia type III pathway (Anderson, et al., *Science,* 278:1140–1143 (1997), which is hereby incorporated by reference). Use of the cloned *Erwinia chrysanthemi* Hrp secretion system should make testing this hypothesis and the identification of targeting signals straightforward.

*Escherichia coli* heterologously expressing the *Erwinia chrysanthemi* Hrp system also can be used to systematically prospect for genes from *Erwinia chrysanthemi, Pseudomonas syringae*, and possibly other bacteria that encode Avr-like effector proteins. However, two factors may limit universal application of this system. First, some Avr-like proteins may require a dedicated chaperone, as has been observed with Yersinia Yops (although characteristic gene arrangements and structural properties of the chaperones may help identify them) (Wattiau, et al., *Mol. Microbiol.,* 20:255–262 (1996), which is hereby incorporated by reference). Second, it is not known whether *Escherichia coli*(pCPP2156) will secrete Avr-like proteins derived from pathogens like *Ralstonia solanacearum* and Xanthomonas spp., which posses group II Hrp systems (Alfano, et al., *J. Bacteriol.,* 179:5655–5662 (1997), which is hereby incorporated by reference).

Example 5

Secretion of DspE by the *Erwinia amylovora* Hrp System

The *Erwinia amylovora* DspE (DspA in Gaudriault et al., *Mol. Microbiol.* 26:1057–1069 (1997), which is hereby incorporate by reference) protein is required for pathogenicity and has homology to AvrE of *Pseudomonas syringae* pv. *tomato* (Bogdanove et al., *Proc. Natl. Acad. Sci. USA* 95:1325–1330 (1998); Gaudriault et al., *Mol. Microbiol.* 26:1057–1069 (1997), which are hereby incorporate by reference). In *Pseudomonas syringae* pv. *glycinia*, DspE acts as an avirulence gene, converting it to avirulence on its host, soybean. In addition, avrE restores pathogenicity to an *Erwinia amylovora* dspE mutant (Bogdanove et al., *Proc. Natl. Acad. Sci. USA* 95:1325–1330 (1998), which is hereby incorporated by reference). Thus, DspE acts as a virulence protein in host plants and as an avirulence protein in a nonhost plant. To determine whether DspE was secreted by the *Erwinia amylovora* Hrp system, strains Ea273 (the wild-type strain), Ea273-K178 (a hrp secretion mutant), and Ea273dspEÆ1521 (containing a 1,521 bp in-frame deletion in the 3' portion of DspE (Bogdanove et al., *J. Bacteriol.* 180:2244–2247 (1998); Bogdanove et al., *Proc. Natl. Acad. Sci. USA* 95:1325–1330 (1998), which are hereby incorporated by reference) were grown in hrp gene-inducing minimal medium. Analysis of the proteins from the cell and supernatant fractions on immunoblots revealed that DspE and DspEÆ1521 were present in the culture supernatant of Ea273 and Ea273dspEÆ1521, respectively (FIG. 6). In contrast, no DspE was detected in the supernatant of the hrp mutant (Ea273-K178), but it was detected within the bacterial cells. Therefore, the DspE protein is secreted in a Hrp-dependent manner.

Example 6

Construction of a Minimal Hrp Secretion and Regulation System

The observations that DspE functions in *Pseudomonas syringae* and that avrE functions in *Erwinia amylovora* raise the possibility that the *Erwinia amylovora* Hrp system functions to secrete other non-Erwinia Avr proteins. This was addressed by preparing *Escherichia coli* containing a minimal functional hrp gene cluster from *Erwinia amylovora* strain 321 and two avirulence genes from *Pseudomonas syringae*. The minimal hrp cluster was constructed to avoid interference by the dsp genes linked to the hrp genes in *Erwinia amylovora* (FIG. 7). A derivative of pCPP430 with the dsp region deleted, was constructed as follows. The partition region of pCPP9 (the vector portion of pCPP430) and the hrpN gene (from pCPP1084, Wei et al., *Science* 257:85–88 (1992), which is hereby incorporated by reference) were cloned into pBluescript II SK-(Stratagene) in the same orientation as in pCPP430. The kanamycin resistance gene from pHP45-Km (Fellay et al., *Gene* 52:147–152 (1987), which is hereby incorporated by reference)was then inserted between the partition region and hrpN. The resulting plasmid was transformed into *Escherichia coli* C2110 (a polAts strain, ref for Tn3HoHo) containing pCPP430. ColE1 based plasmids such as pBluescript cannot replicate in *Escherichia coli* C2110 at the nonpermissive temperature (42° C.), but pSC101 based plasmids such as pCPP9 (the vector portion of pCPP430) can replicate. The resulting strain was grown at 42° C. in medium with spectinomycin (for selection of pCPP430) and kanamycin (for selection of the pBluescript construct). The only way that this can occur is if the pBluescript construct integrates into pCPP430 by homologous recombination between either the partition region, or the hrpN gene. When the temperature is lowered to 30° C., a second recombination event takes place. By selecting for bacterial colonies that are resistant to spectinomycin and kanamycin, but sensitive to ampicillin (the selectable marker in pBluescript II SK-) it was possible to find derivatives of pCPP430 where the entire region of DNA between the partition region of the vector and the hrpN gene was deleted and replaced by the kanamycin resistance gene. The resulting plasmid was named pCPP431. It contains all of the Hrp secretion and regulatory genes, but none of the putative avirulence genes such as dspE.

To be able to regulate the Hrp secretion system without growing the bacteria in hrp gene-inducing minimal medium a second plasmid was constructed. The hrpL gene is an alternate sigma factor that acts as the global regulator of the rest of the hrp genes. hrpL was cloned into pSU21 (Bartolome et al., *Gene* 102:75–78 (1991), which is hereby incorporated by reference) under control of the lac promoter to give pCPP1289. When bacteria containing pCPP1289 and pCPP431 are grown in medium containing IPTG the lac promoter is turned on resulting in production of HrpL protein which then turns on the hrp secretion genes that form the Hrp secretion apparatus.

Example 7

Secretion of *Pseudomonas syringae* Avr Proteins by the *Erwinia amylovora* Hrp System

*Escherichia coli* DH5 containing pCPP430 and pCPP 1289, or pCPP431 and pCPP1289 was used to test the new systems ability to secrete other proteins. *Escherichia coli* DH5 containing pCPP430 with an insertion in hrcV was used as a secretion-defective control. Derivatives of the avirulence genes avrB and avrPto from *Pseudomonas syringae* were constructed in pFLAG-CTC (Sigma) so that the proteins contained the eight-amino-acid FLAG epitope C-terminal fusions to facilitate detection in immunoblots (Ham et al., "A Cloned *Erwinia Chrysanthemi* Hrp (type III Protein Secretion) System Functions in *Escherichia Coli* to Deliver *Pseudomonas syringae* Avr Signals to Plant Cells and to Secrete Avr Proteins in Culture," *Proc. Natl. Acad. Sci. USA*, 95(17): 10206–11 (1998), which is hereby incorporated by reference). The *Escherichia coli* strains described above were transformed with the avrB-FLAG and avrPto-FLAG constructs. Each strain was grown in LB medium, induced with IPTG, and the cultures were separated into cell and supernatant fractions. The proteins from the supernatant were concentrated 50 fold by precipitation with 0.1 volumes of 0.15% deoxycholate and 0.1 volumes of 100% TCA. The precipitated proteins were spun down in a centrifuge, rinsed with acetone and dissolved in PAGE gel loading buffer. The proteins were separated by PAGE, blotted, and the avr proteins detected with antiFLAG monoclonal antibodies (Sigma). AvrB-FLAG and AvrPto-FLAG were present in the cell and supernatant fractions from the strains containing the functional hrp gene clusters, pCPP430 or pCPP431 (FIG. 8). In contrast, the Avr proteins were present within the cells of the strains containing the hrcV mutation in the hrp cluster, but not present in the supernatant. Thus, the secretion is Hrp-dependent. Assay for the cytoplasmic marker (β-galactosidase) revealed nearly imperceptible amounts in the supernatant fractions (not shown). Thus, cell lysis could not account for the presence of the Avr proteins in the supernatant. Therefore, the *Erwinia amylovora* Hrp system is capable of secreting *Pseudomonas syringae* Avr proteins.

Example 8

Secretion of Nonbacterial Proteins

In the Yersinia Yop secretion system the 5'-untranslated portion of the RNA encoding the secreted protein, or the N-terminal portion of the secreted protein contains the signal for secretion through the type secretion system. To test the ability of the *Erwinia amylovora* Hrp secretion system to secrete nonbacterial proteins, a fusion was constructed between the 5'-end of the *Erwinia amylovora* hrpN gene and the mature portion of the human placental alkaline phosphatase gene in the vector pHG 165 (Stewart et al., *Plasmid* 15:172–181 (1986), which is hereby incorporated by reference). The HrpN protein is the main protein secreted by the *Erwinia amylovora* Hrp secretion system. The fusion construct was introduced into *Escherichia coli* DH5 (pCPP431, pCPP 1289) and tested for secretion. The construct was not expressed in the *Escherichia coli* strain. The failure to secrete the fusion protein was apparently due to reasons other than the incompatibility of the HrpN secretion signal with the *Erwinia amylovora* Hrp secretion system.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A DNA construct comprising:
   a first DNA molecule encoding a functional type III secretion system from a first source organism;
   a promoter; and
   a second DNA molecule encoding a protein or polypeptide secreted by the type III secretion system but from a second source organism which is a different species or strain compared to the first source organism, wherein the second DNA molecule is operably coupled to said promoter so that upon introduction of the DNA construct into a host cell which does not naturally express a type III secretion system, the encoded protein or polypeptide and the encoded type III secretion system are expressed and the encoded protein or polypeptide is secreted in culture.

2. The DNA construct according to claim 1, wherein the encoded protein or polypeptide is a fusion protein comprising:
   a secretion signal linked by an in-frame gene fusion to a protein or polypeptide of interest.

3. The DNA construct according to claim 2, wherein the fusion protein further comprises:
   an amino acid sequence between the secretion signal and the protein or polypeptide of interest, which amino acid sequence can be cleaved by a protease.

4. The DNA construct according to claim 2, wherein the secretion signal is a mRNA or a polypeptide fragment of a naturally-occurring protein secreted by the type III secretion system.

5. The DNA construct according to claim 4, wherein the secretion signal is an N-terminal polypeptide fragment of *Erwinia amylovora* DspE.

6. The DNA construct according to claim 5, wherein the N-terminal polypeptide fragment of *Erwinia amylovora* DspE comprises the amino acid sequence of SEQ. ID. No. 1.

7. The DNA construct according to claim 6, wherein the N-terminal polypeptide fragment of *Erwinia amylovora* DspE is encoded by a DNA molecule comprising the nucleotide sequence of SEQ. ID. No. 2.

8. The DNA construct according to claim 1, wherein the first DNA molecule encodes a type III secretion system from *Erwinia amylovora* or *Erwinia chrysanthemi.*

9. The DNA construct according to claim 1, wherein the encoded protein or polypeptide is a naturally-occurring protein or polypeptide.

10. An expression system comprising an expression vector into which is inserted a DNA construct of claim 1.

11. A host cell containing a DNA construct according to claim 1.

12. The host cell according to claim 11, wherein the host cell is present in a cell culture.

13. The host cell according to claim 12, wherein the host cell is a prokaryote.

14. The host cell according to claim 13, wherein the prokaryote is *Escherichia coli.*

15. A system comprising:

a first isolated DNA construct comprising a first DNA molecule encoding a functional type III secretion system and a second isolated DNA construct comprising a promoter operably coupled to a second DNA molecule encoding a protein or polypeptide secreted by the type III secretion system, wherein upon introduction of the first and second DNA constructs into a host cell which does not naturally express a type III secretion system, the encoded protein or polypeptide and the encoded type II secretion system are expressed and the encoded protein or polypeptide is secreted in culture.

16. The system according to claim 15, wherein the first DNA molecule encodes a type III secretion system from *Erwinia amylovora* or *Erwinia chrysanthemi.*

17. The system according to claim 16, wherein the first DNA construct is cosmid pCPP430, which cosmid is present in cells having ATCC Deposit No. PTA-3288.

18. The system according to claim 16, wherein the first DNA construct is cosmid pCPP2156, which cosmid is present in cells having ATCC Deposit No. PTA-3287.

19. The system according to claim 15, wherein the encoded protein or polypeptide is a fusion protein comprising:

a secretion signal linked by an in-frame gene fusion to a protein or polypeptide of interest.

20. The system according to claim 19, wherein the fusion protein further comprises:

an amino acid sequence between the secretion signal and the protein or polypeptide of interest, which amino acid sequence can be cleaved by a protease.

21. The system according to claim 19, wherein the secretion signal is a mRNA or a polypeptide fragment of a naturally-occurring protein secreted by a type III secretion system.

22. The system according to claim 21, wherein the secretion signal is an N-terminal polypeptide fragment of *Erwinia amylovora* DspE.

23. The system according to claim 22, wherein the N-terminal polypeptide fragment of *Erwinia amylovora* DspE comprises the amino acid sequence of SEQ. ID. No. 1.

24. The system according to claim 23, wherein the N-terminal polypeptide fragment of *Erwinia amylovora* DspE is encoded by a DNA molecule comprising the nucleotide sequence of SEQ. ID. No. 2.

25. The system according to claim 15, wherein the encoded protein or polypeptide is a naturally-occurring protein or polypeptide.

26. A host cell containing a system according to claim 15.

27. The host cell according to claim 26, wherein the host cell is present in a cell culture.

28. The host cell according to claim 27, wherein the host cell is a prokaryote.

29. The host cell according to claim 28, wherein the prokaryote is *Escherichia coli*.

30. A method of secreting a protein or polypeptide into the environment of a host cell, said method comprising:
   introducing into a host cell, which does not naturally express a type III secretion system, a DNA construct according to claim 1 under conditions effective to cause expression of the encoded protein or polypeptide and the encoded type III secretion system, wherein the encoded protein or polypeptide is secreted by the host cell into the environment.

31. The method according to claim 30, wherein the encoded protein or polypeptide of interest is a fusion protein comprising:
   a secretion signal linked by an in-frame gene fusion to a protein or polypeptide of interest.

32. The method according to claim 31, wherein the fusion protein further comprises:
   an amino acid sequence between the secretion signal and the protein or polypeptide of interest, which amino acid sequence can be cleaved by a protease.

33. The method according to claim 31, wherein the secretion signal is a mRNA or a polypeptide fragment of a naturally-occurring protein secreted by a type III secretion system.

34. The method according to claim 30, wherein the first DNA molecule encodes a type III secretion system from *Erwinia amylovora* or *Erwinia chrysanthemi*.

35. The method according to claim 30, wherein the encoded protein or polypeptide is a naturally-occurring protein or polypeptide.

36. The method according to claim 30, wherein the host cell is present in a cell culture.

37. The method according to claim 36, wherein the host cell is a prokaryote.

38. The method according to claim 37, wherein the prokaryote is *Escherichia coli*.

39. A method of secreting a protein or polypeptide into the environment of a host cell, said method comprising:
   introducing into a host cell, which does not naturally express a type III secretion system, a system according to claim 15 under conditions effective to cause expression of the encoded protein or polypeptide and the encoded type III secretion system, wherein the encoded protein or polypeptide is secreted by the host cell into the environment.

40. The method according to claim 39, wherein the encoded protein or polypeptide is a fusion protein comprising:
   a secretion signal linked by an in-frame gene fusion to a protein or polypeptide of interest.

41. The method according to claim 40, wherein the fusion protein further comprises:
   an amino acid sequence between the secretion signal and the protein or polypeptide of interest, which amino acid sequence can be cleaved by a protease.

42. The method according to claim 40, wherein the secretion signal is a mRNA or a polypeptide fragment of a naturally-occurring protein secreted by a type III secretion system.

43. The method according to claim 39, wherein the first DNA molecule encodes a type III secretion system from *Erwinia amylovora* or *Erwinia chrysanthemi*.

44. The method according to claim 43, wherein the first DNA construct is cosmid pCPP430, which cosmid is present in cells having ATCC Deposit No. PTA-3288.

45. The method according to claim 43, wherein the first DNA construct is cosmid pCPP2156, which cosmid is present in cells having ATCC Deposit No. PTA-3287.

46. The method according to claim 39, wherein the encoded protein or polypeptide is a naturally-occurring protein or polypeptide.

47. The method according to claim 39, wherein the host cell is present in a cell culture.

48. The method according to claim 47, wherein the host cell is a prokaryote.

49. The method according to claim 48, wherein the prokaryote is *Escherichia coli*.

50. A method of isolating a protein or polypeptide, said method comprising:
   providing a recombinant host cell comprising a first DNA molecule encoding a functional type III secretion system from a first source organism which is a different species or strain compared to the recombinant host cell and a second DNA molecule having a promoter operably coupled to a nucleic acid sequence encoding a protein or polypeptide secreted by the type III secretion system but from a second source organism which is a different species or strain compared to the first source organism;
   introducing the recombinant host cell into a culture medium, wherein the encoded protein or polypeptide and the type III secretion system are expressed and the encoded protein or polypeptide is secreted into the culture medium; and
   isolating the encoded protein or polypeptide from the culture medium.

51. The method according to claim 50, wherein the encoded protein or polypeptide is a fusion protein comprising:
   a secretion signal linked by an in-frame gene fusion to a protein or polypeptide of interest.

52. The method according to claim 51, wherein the fusion protein further comprises:
   an amino acid sequence between the secretion signal and the protein or polypeptide of interest, which amino acid sequence can be cleaved by a protease.

53. The method according to claim 52, wherein said method further comprises:
   introducing into the culture medium, prior to said isolating the encoded protein or polypeptide, a protease which cleaves the amino acid sequence between the secretion signal and the protein or polypeptide of interest.

54. The method according to claim 52, wherein said isolating the encoded protein or polypeptide comprises:
   isolating the fusion protein from the culture medium;
   exposing the isolated fusion protein to a protease which cleaves the amino acid sequence between the secretion signal and the protein or polypeptide of interest; and
   recovering the protein or polypeptide of interest.

55. The method according to claim 51, wherein the secretion signal is a mRNA or a polypeptide fragment of a naturally-occurring protein secreted by a type III secretion system.

56. The method according to claim 50, wherein the type III secretion system is a type III secretion system from *Erwinia amylovora* or *Erwinia chrysanthemi*.

57. The method according to claim 50, wherein the first DNA molecule is cosmid pCPP430, which cosmid is present in cells having ATCC Deposit No. PTA-3288.

58. The method according to claim 50, wherein the first DNA molecule is cosmid pCPP2156, which cosmid is present in cells having ATCC Deposit No. PTA-3287.

59. The method according to claim 50, wherein the encoded protein or polypeptide is a naturally-occurring protein or polypeptide.

60. The method according to claim 50, wherein the host cell is *Escherichia coli*.

61. A method of determining whether a gene encodes a potential effector protein or polypeptide comprising:
providing a recombinant host cell comprising a DNA molecule encoding a functional type III secretion system from a source organism which is a different species or strain compared to the recombinant host cell;
introducing into the recombinant host cell a candidate gene encoding a protein or polypeptide under conditions effective to express the encoded protein or polypeptide; and
determining whether the encoded protein or polypeptide is secreted in culture by the recombinant host cell, wherein secretion of the encoded protein or polypeptide is indicative of the candidate gene encoding a potential effector protein or polypeptide.

62. The method according to claim 61, wherein the recombinant host cell is *Escherichia coli*.

63. The method according to claim 61, wherein the type III protein secretion system is a type III protein secretion system of *Erwinia amylovora* or *Erwinia chrysanthemi*.

64. The method according to claim 61, said method further comprising:
introducing the DNA molecule into the recombinant host cell.

65. The method according to claim 64, wherein the DNA molecule is cosmid pCPP430, which cosmid is present in cells having ATCC Deposit No. PTA-3288, or cosmid pCPP2156, which cosmid is present in cells having ATCC Deposit No. PTA-3287.

66. The method according to claim 61, wherein the gene is a chimeric gene encoding an epitope tag fused to the encoded protein or polypeptide and said determining comprises:
isolating all protein or polypeptide products secreted by the recombinant host cell;
exposing the isolated protein or polypeptide products to an antibody recognizing the epitope tag; and
detecting any antibody bound to the encoded protein or polypeptide.

67. The DNA construct according to claim 4, wherein the secretion signal is a mRNA.

68. The system according to claim 21, wherein the secretion signal is a mRNA.

69. A DNA construct consisting essentially of:
a first DNA molecule encoding a functional type III secretion system;
a promoter; and
a second DNA molecule encoding a protein or polypeptide secreted by the encoded type III secretion system, wherein the second DNA molecule is operably coupled to said promoter so that upon introduction of the DNA construct into a host cell which does not naturally express a type III secretion system, the encoded protein or polypeptide and the encoded type III secretion system are expressed and the encoded protein or polypeptide is secreted in culture.

70. The DNA construct according to claim 69, wherein the encoded protein or polypeptide is a fusion protein comprising:
a secretion signal linked by an in-frame gene fusion to a protein or polypeptide of interest.

71. The DNA construct according to claim 69, wherein the first DNA molecule encodes a type III secretion system from *Erwinia amylovora* or *Erwinia chrysanthemi*.

72. The DNA construct according to claim 69, wherein the encoded protein or polypeptide is a naturally-occurring protein or polypeptide.

73. An expression system comprising an expression vector into which is inserted a DNA construct of claim 69.

74. A host cell containing a DNA construct according to claim 69.

75. A method of secreting a protein or polypeptide into the environment of a host cell, said method comprising:
introducing into a host cell, which does not naturally express a type III secretion system, a DNA construct according to claim 69, under conditions effective to cause expression of the encoded protein or polypeptide and the type III secretion system, wherein the encoded protein or polypeptide is secreted by the host cell into the environment.

76. The method according to claim 75, wherein the encoded protein or polypeptide is a fusion protein comprising:
a secretion signal linked by an in-frame gene fusion to a protein or polypeptide of interest.

77. The method according to claim 76, wherein the fusion protein further comprises:
an amino acid sequence between the secretion signal and the protein or polypeptide of interest, which amino acid sequence can be cleaved by a protease.

78. The method according to claim 76, wherein the secretion signal is a mRNA or a polypeptide fragment of a naturally-occurring protein secreted by a type III secretion system.

79. The method according to claim 75, wherein the first DNA molecule encodes a type III secretion system from *Erwinia amylovora* or *Erwinia chrysanthemi*.

80. The method according to claim 75, wherein the encoded protein or polypeptide is a naturally-occurring protein or polypeptide.

81. A method of isolating a protein or polypeptide, said method comprising:
providing a recombinant host cell comprising a first DNA molecule encoding a functional type III secretion system from a first source organism which is a different species compared to the recombinant host cell and a second DNA molecule having a promoter operably coupled to a nucleic acid sequence encoding a protein or polypeptide secreted by the type III secretion system;
introducing the recombinant host cell into a culture medium, wherein the encoded protein or polypeptide and the type III secretion system are expressed and the encoded protein or polypeptide is secreted into the culture medium; and
isolating the encoded protein or polypeptide from the culture medium.

82. The method according to claim 81, wherein the encoded protein or polypeptide is a fusion protein comprising:
a secretion signal linked by an in-frame gene fusion to a protein or polypeptide of interest.

83. The method according to claim 82, wherein the fusion protein further comprises:
an amino acid sequence between the secretion signal and the protein or polypeptide of interest, which amino acid sequence can be cleaved by a protease.

84. The method according to claim 83, wherein said method further comprises:

introducing into the culture medium, prior to said isolating the encoded protein or polypeptide, a protease which cleaves the amino acid sequence between the secretion signal and the protein or polypeptide of interest.

85. The method according to claim 83, wherein said isolating the encoded protein or polypeptide comprises:

isolating the fusion protein from the culture medium;

exposing the isolated fusion protein to a protease which cleaves the amino acid sequence between the secretion signal and the protein or polypeptide of interest; and recovering the protein or polypeptide of interest.

86. The method according to claim 82, wherein the secretion signal is a mRNA or a polypeptide fragment of a naturally-occurring protein secreted by a type III secretion system.

87. The method according to claim 81, wherein the type III secretion system is a type III secretion system from *Erwinia amylovora* or *Erwinia chrysanthemi*.

88. The method according to claim 81, wherein the encoded protein or polypeptide is a naturally-occurring protein or polypeptide.

89. The method according to claim 81, wherein the host cell is *Escherichia coli*.

90. The system according to claim 25, wherein the protein or polypeptide and the type III secretion system are from different species of source organisms.

91. The method according to claim 46, wherein the protein or polypeptide and the type III secretion system are from different species of source organisms.

* * * * *